United States Patent
Parisi et al.

(10) Patent No.: US 8,591,594 B2
(45) Date of Patent: Nov. 26, 2013

(54) MOTION FACILITATING TIBIAL COMPONENTS FOR A KNEE PROSTHESIS

(75) Inventors: Raymond C. Parisi, Wakarusa, IN (US); Katherine M. Rettig, Cincinnati, OH (US); Jeff C. Blaylock, Fort Wayne, IN (US)

(73) Assignee: Zimmer, Inc., Warsaw, IN (US)

( * ) Notice: Subject to any disclaimer, the term of this patent is extended or adjusted under 35 U.S.C. 154(b) by 94 days.

(21) Appl. No.: 13/229,103

(22) Filed: Sep. 9, 2011

(65) Prior Publication Data
US 2012/0101585 A1    Apr. 26, 2012

Related U.S. Application Data

(60) Provisional application No. 61/381,800, filed on Sep. 10, 2010.

(51) Int. Cl.
*A61F 2/38* (2006.01)
(52) U.S. Cl.
USPC ..................................... 623/20.32; 623/20.21
(58) Field of Classification Search
USPC .......................................... 623/20.21, 20.32
See application file for complete search history.

(56) References Cited

U.S. PATENT DOCUMENTS

| | | | |
|---|---|---|---|
| 4,340,978 A | 7/1982 | Buechel et al. | |
| 4,714,474 A | 12/1987 | Brooks, Jr. et al. | |
| 4,769,040 A | 9/1988 | Wevers | |
| 4,770,661 A | 9/1988 | Oh | |
| 4,795,468 A | 1/1989 | Hodorek et al. | |
| 4,822,365 A | 4/1989 | Walker et al. | |
| 4,936,853 A | 6/1990 | Fabian et al. | |
| 4,950,298 A | 8/1990 | Gustilo et al. | |
| 4,959,071 A | 9/1990 | Brown et al. | |
| 4,963,152 A | 10/1990 | Hofmann et al. | |
| 5,047,058 A | 9/1991 | Roberts et al. | |

(Continued)

FOREIGN PATENT DOCUMENTS

| | | |
|---|---|---|
| CN | 103118634 A | 5/2013 |
| CN | 103118635 A | 5/2013 |

(Continued)

OTHER PUBLICATIONS

Product Brochure—Zimmer Gender Solutions Natural-Knee Flex System, Zimmer, Inc. 2007, 2009.

(Continued)

*Primary Examiner* — Bruce E Snow
*Assistant Examiner* — Brian Dukert
(74) *Attorney, Agent, or Firm* — Schwegman, Lundberg & Woessner P.A.

(57) ABSTRACT

An orthopaedic tibial prosthesis includes a tibial baseplate sized and shaped to cover substantially all of a resected proximal tibial surface, and a tibial bearing component sized to leave a posteromedial portion of the tibial baseplate exposed when the tibial bearing component is mounted to the baseplate. The exposed posteromedial portion of the tibial baseplate includes a chamfered profile which cooperates with a correspondingly chamfered profile at a posteromedial edge of the tibial bearing component to create a substantially continuous chamfer extending from the resected tibial surface to the medial articular surface of the tibial bearing component. Advantageously, this chamfer leaves an absence of material (i.e., a relief or void) at the posteromedial edge of the tibial prosthesis, thereby enabling deep flexion of the prosthesis without impingement between the tibial prosthesis and adjacent anatomic tissues or prosthetic structures.

31 Claims, 10 Drawing Sheets

(56) References Cited

U.S. PATENT DOCUMENTS

| | | |
|---|---|---|
| 5,061,271 A | 10/1991 | Van Zile |
| 5,071,438 A | 12/1991 | Jones et al. |
| 5,133,758 A | 7/1992 | Hollister |
| 5,137,536 A | 8/1992 | Koshino |
| 5,192,328 A | 3/1993 | Winters |
| 5,236,461 A | 8/1993 | Forte |
| 5,246,459 A | 9/1993 | Elias |
| 5,271,737 A | 12/1993 | Baldwin et al. |
| 5,282,861 A | 2/1994 | Kaplan |
| 5,282,868 A | 2/1994 | Bahler |
| 5,282,870 A | 2/1994 | Moser et al. |
| 5,290,313 A | 3/1994 | Heldreth |
| 5,310,480 A | 5/1994 | Vidueira |
| 5,326,361 A | 7/1994 | Hollister |
| 5,344,460 A | 9/1994 | Turanyi et al. |
| 5,370,699 A | 12/1994 | Hood et al. |
| 5,405,396 A | 4/1995 | Heldreth et al. |
| 5,413,604 A | 5/1995 | Hodge |
| 5,413,605 A | 5/1995 | Ashby et al. |
| 5,507,820 A | 4/1996 | Pappas |
| 5,549,688 A | 8/1996 | Ries et al. |
| 5,556,433 A | 9/1996 | Gabriel et al. |
| 5,609,639 A | 3/1997 | Walker |
| 5,609,641 A | 3/1997 | Johnson et al. |
| 5,609,645 A | 3/1997 | Vinciguerra |
| 5,613,970 A | 3/1997 | Houston et al. |
| 5,658,344 A | 8/1997 | Hurlburt |
| 5,755,802 A | 5/1998 | Gerber |
| 5,824,100 A | 10/1998 | Kester et al. |
| 5,824,102 A | 10/1998 | Buscayret |
| 5,871,539 A | 2/1999 | Pappas |
| 5,879,394 A | 3/1999 | Ashby et al. |
| 5,928,286 A | 7/1999 | Ashby et al. |
| 5,964,808 A | 10/1999 | Blaha et al. |
| 6,004,351 A | 12/1999 | Tomita et al. |
| 6,013,103 A | 1/2000 | Kaufman et al. |
| 6,039,764 A | 3/2000 | Pottenger et al. |
| 6,068,658 A | 5/2000 | Insall et al. |
| 6,074,425 A | 6/2000 | Pappas |
| 6,090,144 A | 7/2000 | Letot et al. |
| 6,102,954 A | 8/2000 | Albrektsson et al. |
| 6,102,955 A | 8/2000 | Mendes et al. |
| 6,197,064 B1 | 3/2001 | Haines et al. |
| 6,203,576 B1 | 3/2001 | Afriat et al. |
| 6,206,927 B1 | 3/2001 | Fell et al. |
| RE37,277 E | 7/2001 | Baldwin et al. |
| 6,258,127 B1 | 7/2001 | Schmotzer |
| 6,306,172 B1 | 10/2001 | O'Neil et al. |
| 6,379,388 B1 | 4/2002 | Ensign et al. |
| 6,413,279 B1 | 7/2002 | Metzger et al. |
| 6,491,726 B2 | 12/2002 | Pappas |
| 6,506,216 B1 | 1/2003 | McCue et al. |
| 6,709,461 B2 | 3/2004 | O'Neil et al. |
| 6,770,078 B2 | 8/2004 | Bonutti |
| 6,869,448 B2 | 3/2005 | Tuke |
| 6,923,832 B1 | 8/2005 | Sharkey et al. |
| 6,953,479 B2 | 10/2005 | Carson et al. |
| 6,986,791 B1 | 1/2006 | Metzger |
| 7,025,788 B2 | 4/2006 | Metzger et al. |
| 7,083,652 B2 | 8/2006 | McCue et al. |
| 7,153,326 B1 | 12/2006 | Metzger |
| 7,189,262 B2 | 3/2007 | Hayes, Jr. et al. |
| 7,264,635 B2 | 9/2007 | Suguro |
| 7,294,149 B2 | 11/2007 | Hozack et al. |
| 7,309,362 B2 | 12/2007 | Yasuda et al. |
| 7,445,639 B2 | 11/2008 | Metzger et al. |
| 7,497,874 B1 | 3/2009 | Metzger et al. |
| 7,513,912 B2 | 4/2009 | Hayes, Jr. et al. |
| 7,544,211 B2 | 6/2009 | Rochetin |
| 7,585,328 B2 | 9/2009 | Haas |
| 7,625,407 B2 | 12/2009 | Akizuki |
| 7,628,818 B2 | 12/2009 | Hazebrouck et al. |
| 7,635,390 B1 | 12/2009 | Bonutti |
| 7,695,519 B2 | 4/2010 | Collazo |
| 7,850,698 B2 | 12/2010 | Straszheim-Morley et al. |
| 2002/0072802 A1* | 6/2002 | O'Neil et al. ............... 623/20.33 |
| 2002/0120340 A1 | 8/2002 | Metzger et al. |
| 2004/0034432 A1 | 2/2004 | Hughes et al. |
| 2004/0153066 A1 | 8/2004 | Coon et al. |
| 2004/0162620 A1* | 8/2004 | Wyss .......................... 623/20.27 |
| 2004/0186582 A1 | 9/2004 | Yasuda et al. |
| 2004/0267371 A1 | 12/2004 | Hayes, Jr. et al. |
| 2005/0096747 A1 | 5/2005 | Tuttle et al. |
| 2005/0143831 A1 | 6/2005 | Justin et al. |
| 2005/0143832 A1 | 6/2005 | Carson |
| 2005/0209702 A1 | 9/2005 | Todd et al. |
| 2005/0267584 A1 | 12/2005 | Burdulis et al. |
| 2006/0030945 A1 | 2/2006 | Wright |
| 2006/0142869 A1 | 6/2006 | Gross |
| 2006/0161259 A1 | 7/2006 | Cheng et al. |
| 2006/0195195 A1 | 8/2006 | Burstein et al. |
| 2006/0224244 A1 | 10/2006 | Thomas et al. |
| 2007/0010890 A1 | 1/2007 | Collazo |
| 2007/0135926 A1 | 6/2007 | Walker |
| 2007/0198022 A1 | 8/2007 | Lang et al. |
| 2007/0233269 A1 | 10/2007 | Steines et al. |
| 2008/0021566 A1 | 1/2008 | Peters et al. |
| 2008/0051908 A1 | 2/2008 | Angibaud et al. |
| 2008/0091271 A1 | 4/2008 | Bonitati et al. |
| 2008/0091272 A1 | 4/2008 | Aram et al. |
| 2008/0091273 A1 | 4/2008 | Hazebrouck |
| 2008/0114462 A1 | 5/2008 | Guidera et al. |
| 2008/0167722 A1 | 7/2008 | Metzger et al. |
| 2008/0215156 A1 | 9/2008 | Duggal et al. |
| 2008/0243258 A1 | 10/2008 | Sancheti |
| 2008/0281426 A1 | 11/2008 | Fitz et al. |
| 2008/0288080 A1 | 11/2008 | Sancheti |
| 2009/0036992 A1 | 2/2009 | Tsakonas |
| 2009/0082873 A1 | 3/2009 | Hazebrouck et al. |
| 2009/0088862 A1 | 4/2009 | Thomas et al. |
| 2009/0125114 A1 | 5/2009 | May et al. |
| 2009/0149963 A1 | 6/2009 | Sekel |
| 2009/0149964 A1 | 6/2009 | May et al. |
| 2009/0204222 A1 | 8/2009 | Burstein et al. |
| 2009/0222103 A1 | 9/2009 | Fitz et al. |
| 2009/0306786 A1 | 12/2009 | Samuelson |
| 2009/0319047 A1 | 12/2009 | Walker |
| 2010/0016978 A1 | 1/2010 | Williams et al. |
| 2010/0016979 A1 | 1/2010 | Wyss et al. |
| 2010/0063594 A1 | 3/2010 | Hazebrouck et al. |
| 2010/0100189 A1* | 4/2010 | Metzger .................... 623/20.14 |
| 2010/0125339 A1 | 5/2010 | Earl et al. |
| 2010/0152858 A1 | 6/2010 | Lu et al. |
| 2010/0191341 A1 | 7/2010 | Byrd |
| 2010/0222890 A1 | 9/2010 | Barnett et al. |
| 2010/0305708 A1 | 12/2010 | Lang |
| 2010/0329530 A1 | 12/2010 | Lang et al. |
| 2011/0082559 A1 | 4/2011 | Hartdegen et al. |
| 2011/0144760 A1 | 6/2011 | Wong et al. |
| 2012/0022658 A1 | 1/2012 | Wentorf |
| 2012/0022659 A1 | 1/2012 | Wentorf |
| 2012/0022660 A1 | 1/2012 | Wentorf |
| 2012/0035735 A1 | 2/2012 | Sanford et al. |
| 2012/0035737 A1 | 2/2012 | Sanford |
| 2013/0024001 A1 | 1/2013 | Wentorf et al. |
| 2013/0131820 A1 | 5/2013 | Wentorf et al. |

FOREIGN PATENT DOCUMENTS

| | | |
|---|---|---|
| CN | 103118636 A | 5/2013 |
| EP | 0021421 A1 | 1/1981 |
| EP | 0340919 A1 | 11/1989 |
| EP | 0372811 A1 | 6/1990 |
| EP | 0306744 B1 | 4/1992 |
| EP | 0495340 A1 | 7/1992 |
| EP | 0672397 A1 | 9/1995 |
| EP | 0552950 B1 | 9/1996 |
| EP | 0536457 B1 | 1/1997 |
| EP | 0642328 B1 | 12/1998 |
| EP | 0956836 A1 | 11/1999 |
| EP | 0956836 B1 | 11/1999 |
| EP | 1097679 A1 | 5/2001 |
| EP | 0709074 B1 | 12/2002 |
| EP | 1327424 A1 | 7/2003 |

(56) References Cited

FOREIGN PATENT DOCUMENTS

| | | | |
|---|---|---|---|
| EP | 1396240 B1 | 4/2008 |
| EP | 1996122 A1 | 12/2008 |
| EP | 0927009 B1 | 1/2009 |
| EP | 1555962 B1 | 2/2011 |
| EP | 2319460 A1 | 5/2011 |
| EP | 2324799 A2 | 5/2011 |
| EP | 2335654 A1 | 6/2011 |
| EP | 2347733 A1 | 7/2011 |
| EP | 0689808 B1 | 9/2012 |
| FR | 2736819 A1 | 1/1997 |
| FR | 2747914 A1 | 10/1997 |
| FR | 2778332 A1 | 11/1999 |
| FR | 2788964 A1 | 8/2000 |
| FR | 2926719 A1 | 7/2009 |
| GB | 2253147 A | 9/1992 |
| GB | 2345446 A | 7/2000 |
| WO | WO-9305729 A2 | 4/1993 |
| WO | WO-9409725 A1 | 5/1994 |
| WO | WO-9514444 A1 | 6/1995 |
| WO | WO95/30389 A1 | 11/1995 |
| WO | WO-9535074 A1 | 12/1995 |
| WO | WO-9934755 A1 | 7/1999 |
| WO | WO-0141680 A1 | 6/2001 |
| WO | WO-03099106 A2 | 12/2003 |
| WO | WO2005/037147A1 A1 | 4/2005 |
| WO | WO-2005051240 A1 | 6/2005 |
| WO | WO-2006058057 A2 | 6/2006 |
| WO | WO-2007108804 A1 | 9/2007 |
| WO | WO-2007109641 A2 | 9/2007 |
| WO | WO-2009029631 A1 | 3/2009 |
| WO | WO2009/088238 A2 | 7/2009 |
| WO | WO-2010008803 A2 | 1/2010 |
| WO | WO-2010045537 A1 | 4/2010 |
| WO | WO-2011072235 A2 | 6/2011 |
| WO | WO2012/018563 A1 | 2/2012 |
| WO | WO2012/018564 A1 | 2/2012 |
| WO | WO2012/018565 A1 | 2/2012 |
| WO | WO2012/018566A1 A1 | 2/2012 |
| WO | WO2012/018567A1 A1 | 2/2012 |
| WO | WO-2012112698 A2 | 8/2012 |
| WO | WO-2013077919 A1 | 5/2013 |

OTHER PUBLICATIONS

International Search Report and Written Opinion mailed Nov. 23, 2011 in related International Application No. PCT/US2011/051021.
Design Rationale, Smith & Nephew Journal, Bi-Cruciate Stabilized Knee System, Smith & Nephew 2006.
Tibial Insertion of the Posterior Cruciate Ligament: A Sagittal Plane Analysis Using Gross, Histologic, and Radiographic Methods, Claude Moorman III et al., Arthroscopy: The Journal of Arthroscopic and Related Surgery, vol. 24, No. 3, Mar. 2008, pp. 269-275.
The Attachments of the Fiber Bundles of the Posterior Cruciate Ligament: An Anatomic Study, Andrew Edwards et al., Arthroscopy: The Journal of Arthroscopic and Related Surgery, vol. 23, No. 7, Mar. 2007, pp. 284-290.
Radiological evaluation of the anterolateral and posteromedial bundle insertion sites of the posterior cruciate ligament, Stephan Lorenz et al., Knee Surg Sports Traumatol Arthosc (2009) 17, pp. 683-690.
CR Flex, Zimmer NexGen Complete Knee Solution, Surgical Technique for the CR-Flex Fixed Bearing Knee, Zimmer, Inc. 2003.
Zimmer NexGen Complete Knee Solution Extramedullary/Intramedullary Tibial Resector Surgical Technique, Zimmer, Inc. 2000, 2008, 2009.
Zimmer LPS-Flex Fixed Bearing Knee Surgical Technique, Zimmer 2004, 2007, 2008.
"U.S. Appl. No. 13/189,324, Final Office Action mailed Jul. 16, 2013", 19 pgs.
"U.S. Appl. No. 13/189,324, Non Final Office Action mailed Dec. 11, 2012", 19 pgs.
"U.S. Appl. No. 13/189,324, Response filed Jun. 10, 2013 to Non Final Office Action mailed Dec. 11, 2012", 24 pgs.
"U.S. Appl. No. 13/189,328, Non Final Office Action mailed Mar. 19, 2013", 10 pgs.
"U.S. Appl. No. 13/189,328, Response filed Jan. 10, 2013 to Restriction Requirement mailed Dec. 10, 2012", 9 pgs.
"U.S. Appl. No. 13/189,328, Response filed Jul. 18, 2013 to Non Final Office Action mailed Mar. 19, 2013", 16 pgs.
"U.S. Appl. No. 13/189,328, Restriction Requirement mailed Dec. 10, 2012", 6 pgs.
"U.S. Appl. No. 13/189,336, Response filed Apr. 15, 2013 to Restriction Requirement mailed Jan. 30, 2013", 21 pgs.
"U.S. Appl. No. 13/189,336, Response filed Jul. 17, 2013 to Restriction Requirement mailed Jun. 17, 2013", 20 pgs.
"U.S. Appl. No. 13/189,336, Restriction Requirement mailed Jan. 30, 2013", 5 pgs.
"U.S. Appl. No. 13/189,336, Restriction Requirement mailed Jun. 17, 2013", 6 pgs.
"U.S. Appl. No. 13/189,338, Response filed Apr. 15, 2013 to Restriction Requirement mailed Feb. 14, 2013", 18 pgs.
"U.S. Appl. No. 13/189,338, Response filed Jul. 17, 2013 to Restriction Requirement mailed Jun. 17, 2013", 16 pgs.
"U.S. Appl. No. 13/189,338, Restriction Requirement mailed Feb. 14, 2013", 5 pgs.
"U.S. Appl. No. 13/189,338, Restriction Requirement mailed Jun. 17, 2013", 6 pgs.
"U.S. Appl. No. 13/189,339, Response filed Apr. 15, 2013 to Restriction Requirement mailed Mar. 6, 2013", 11 pgs.
"U.S. Appl. No. 13/189,339, Response filed Jul. 17, 2013 to Restriction Requirement mailed Jun. 17, 2013", 10 pgs.
"U.S. Appl. No. 13/189,339, Restriction Requirement mailed Mar. 6, 2013", 6 pgs.
"U.S. Appl. No. 13/189,339, Restriction Requirement mailed Jun. 17, 2013", 7 pgs.
"U.S. Appl. No. 13/593,339, Preliminary Amendment filed Aug. 23, 2012", 6 pgs.
"U.S. Appl. No. 13/594,543, Preliminary Amendment filed Aug. 24, 2012", 4 pgs.
"Extramedullary/Intramedullary Tibial Resector: Surgical Technique", Nexgen Complete Knee Solution, Zimmer, Inc., (2000, 2008, 2009), 28 pgs.
"International Application Serial No. PCT/US2011/045077, International Preliminary Report on Patentability mailed Jul. 5, 2012", 23 pgs.
"International Application Serial No. PCT/US2011/045077, International Search Report and Written Opinion mailed Jan. 9, 2012", 15 pgs.
"International Application Serial No. PCT/US2011/045078, International Preliminary Report on Patentability mailed Feb. 7, 2013", 11 pgs.
"International Application Serial No. PCT/US2011/045078, International Search Report and Written Opinion mailed Jan. 9, 2012", 14 pgs.
"International Application U.S. Appl. No. PCT/US2011/045080, International Preliminary Report on Patentability mailed 02-07-13", 13 pgs.
"International Application Serial No. PCT/US2011/045080, International Search Report mailed Jan. 9, 2012", 7 pgs.
"International Application Serial No. PCT/US2011/045080, Written Opinion mailed Jan. 9, 2012", 11 pgs.
"International Application Serial No. PCT/US2011/045082, International Preliminary Report on Patentability mailed Feb. 7, 2013", 11 pgs.
"International Application Serial No. PCT/US2011/045082, International Search Report mailed Jan. 9, 2012", 5 pgs.
"International Application Serial No. PCT/US2011/045082, Written Opinion mailed Jan. 9, 2012", 10 pgs.
"International Application Serial No. PCT/US2011/045083, International Preliminary Report on Patentability mailed Feb. 7, 2013", 8 pgs.
"International Application Serial No. PCT/US2011/045083, International Search Report mailed Dec. 7, 2011", 2 pgs.
"International Application Serial No. PCT/US2011/045083, Written Opinion mailed Dec. 7, 2011", 6 pgs.

(56) References Cited

OTHER PUBLICATIONS

"International Application Serial No. PCT/US2011/051021, International Preliminary Report on Patentability mailed Mar. 21, 2013", 8 pgs.

"International Application Serial No. PCT/US2012/052132, International Search Report mailed Jan. 10, 2013", 5 pgs.

"International Application Serial No. PCT/US2012/052132, Invitation to Pay Additional Fees and Partial Search Report mailed Nov. 15, 2012", 7 pgs.

"International Application Serial No. PCT/US2012/052132, Written Opinion mailed Jan. 10, 2013", 10 pgs.

"Tibial Baseplate: Pocket Guide (United States Version)", Zimmer, Inc. (2009), 17 pgs.

Dunbar, M. J., et al., "Fixation of a Trabecular Metal Knee Arthroplasty Component: a Prospective Randomized Study", The Journal of Bone & Joint Surgery (American), vol. 91A(7), (Jul. 2009), 1578-1586.

Parisi, Raymond C, "Motion Facilitating Tibial Components for a Knee Prosthesis", US Application U.S. Appl. No. 13/229,103, filed 09-09-11, 46 pgs.

"International Application Serial No. PCT/US2012/052340, Search Report mailed Oct. 12, 2012", 4 pgs.

"International Application Serial No. PCT/US2012/052340, Written Opinion mailed Oct. 12, 2012", 6 pgs.

"NexGen Trabecular Metal Modular Plates", Zimmer Inc., (2007), 19 pgs.

"Tibial Baseplate: Pocket Guide (United States Version)", Zimmer, Inc., (2009), 17 pgs.

"Trabecular Metal Monoblock Tibial Components", Zimmer, Inc., (2007), 4 pgs.

"Trabecular Metal Monoblock Tibial Components Surgical Technique Addendum", Nexgen Zimmer, Inc., (2005, 2007), 12.

"Trabecular Metal Tibial Tray: Surgical Technique", NexGen Zimmer, Inc., (2007, 2009), 16 pgs.

Annayappa, Ramesh, "Tibial Prosthesis", U.S. Appl. No. 13/189,328, filed Jul. 22, 2011, 82 pgs.

Annayappa, Ramesh, et al., "Tibial Prosthesis", U.S. Appl. No. 13/189,324, filed Jul. 22, 2011, 50 pgs.

Ding, M., et al., "Age-related variations in the microstructure of human tibial cancellous bone", Journal of Orthopaedic Research, 20(3), (2002), 615-621.

Ding, M., et al., "Changes in the three-dimensional microstructure of human tibial cancellous bone in early osteoarthritis", Journal of Bone & Joint Surgery (British), 85-B(6), (Aug. 2003), 906-912.

Doyle, et al., "Comparative Analysis of Human Trabecular Bone and Polyurethane Foam", Purdue University., 1 pg.

Dunbar, M. J., et al., "Fixation of a Trabecular Metal Knee Arthroplasty Component: A Prospective Randomized Study", The Journal of Bone & Joint Surgery (American), vol. 91-A(7), (Jul. 2009), 1578-1586.

Hvid, Ivan, et al., "Trabecular bone Strength Patterns at the Proximal Tibial Epiphysis", Journal of Orthopaedic Research, vol. 3, No. 4, (1985), 464-472.

Klostermann, et al., "Distribution of bone mineral density with age and gender in the proximal tibia", Clinical Biomechanics 19, 376-376.

Parisi, Raymond C, "Motion Facilitating Tibial Components for a Knee Prosthesis", U.S. Appl. No. 13/229,103, filed Sep. 9, 2011, 46 pgs.

Stilling, et al., "Superior fixation of pegged trabecular metal over screw-fixed pegged porous titanium fiber mesh", Acta Orthopaedica., (2011), 177-186.

\* cited by examiner

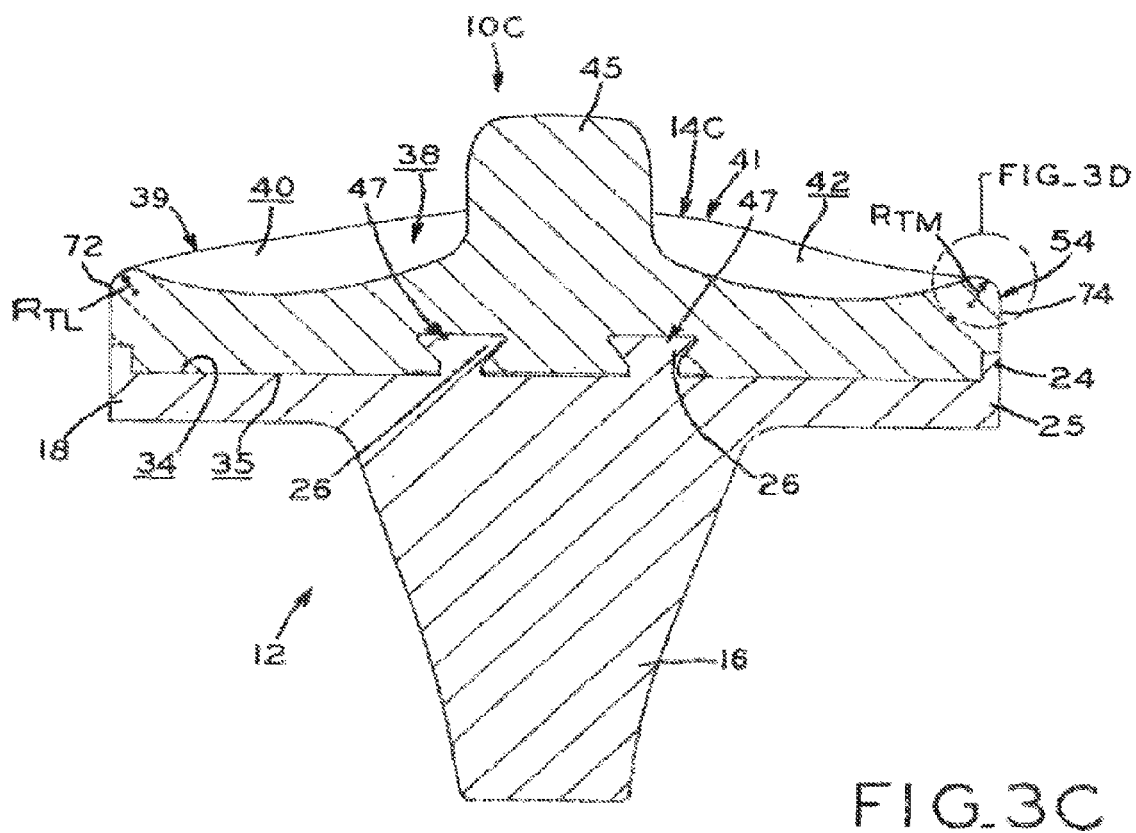
FIG_3C
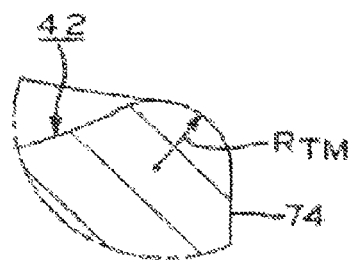
FIG_3D

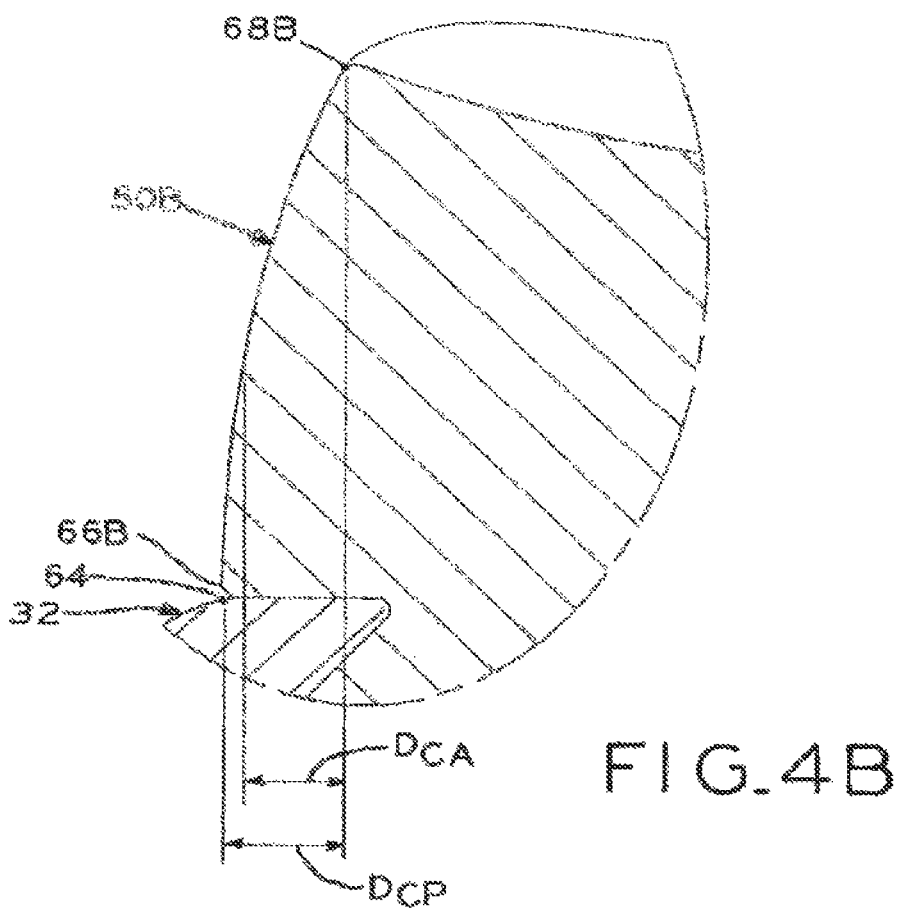

MOTION FACILITATING TIBIAL COMPONENTS FOR A KNEE PROSTHESIS

CROSS-REFERENCE TO RELATED APPLICATIONS

This application claims the benefit under Title 35, U.S.C. §119(e) of U.S. Provisional Patent Application Ser. No. 61/381,800, filed on Sep. 10, 2010 and entitled TIBIAL PROSTHESIS FACILITATING ROTATIONAL ALIGNMENT, the entire disclosure of which is hereby expressly incorporated by reference herein.

BACKGROUND

1. Technical Field

The present disclosure relates to orthopaedic prostheses and, specifically, to tibial components in a knee prosthesis.

2. Description of the Related Art

Orthopaedic prostheses are commonly utilized to repair and/or replace damaged bone and tissue in the human body. For example, a knee prosthesis used in total knee arthroplasty may include a tibial baseplate that is affixed to a resected or natural proximal tibia, a femoral component attached to a resected or natural distal femur, and a tibial bearing component coupled with the tibial baseplate and disposed between the tibial baseplate and femoral component. Knee prostheses frequently seek to provide articulation similar to a natural, anatomical articulation of a knee joint, including providing a wide range of flexion.

The tibial bearing component, sometimes also referred to as a tibial insert or meniscal component, is used to provide an appropriate level of constraint and conformity at the interface between the femoral component and the tibial bearing component. For a knee prosthesis to provide a sufficient range of flexion with a desirable kinematic motion profile, the tibial bearing component and tibial baseplate must be sized and oriented to interact appropriately with the femoral component of the knee prosthesis throughout the flexion range. Substantial design efforts have focused on providing a range of prosthesis component sizes and shapes to accommodate the natural variability in bone sizes and shapes in patients with orthopaedic prostheses, while preserving flexion range and desired kinematic motion profile.

In addition to facilitating implantation and providing enhanced kinematics through manipulation of the size and/or geometry of prosthesis components, protection and/or preservation of soft tissues in the natural knee joint is also desirable.

A given prosthetic component design (i.e., a tibial baseplate, tibial bearing component, or femoral component) may be provided to a surgeon as a kit including a variety of different sizes, so that the surgeon may choose an appropriate size intraoperatively and/or on the basis of pre-surgery planning. An individual component may be selected from the kit based upon the surgeon's assessment of fit and kinematics, i.e., how closely the component matches the natural contours of a patient's bone and how smoothly the assembled knee joint prosthesis functions in conjunction with adjacent soft tissues and other anatomical structures. Soft tissue considerations include proper ligament tension and minimization of soft tissue impingement upon prosthetic surfaces, for example.

In addition to prosthetic sizing, the orientation of a prosthetic component on a resected or natural surface of a bone also impacts surgical outcomes. For example, the rotational orientation of a tibial baseplate and tibial bearing component with respect to a resected proximal tibia will affect the interaction between the corresponding femoral prosthesis and the tibial bearing component. Thus, substantial design efforts have been focused on providing prosthetic components which are appropriately sized for a variety of patient bone sizes and are adapted to be implanted in a particular, proper orientation to achieve desired prosthesis performance characteristics.

SUMMARY

The present disclosure provides an orthopaedic tibial prosthesis including a tibial baseplate sized and shaped to cover substantially all of a resected proximal tibial surface, and a tibial bearing component sized to leave a posteromedial portion of the tibial baseplate exposed when the tibial bearing component is mounted to the baseplate. The exposed posteromedial portion of the tibial baseplate includes a chamfered profile which cooperates with a correspondingly chamfered profile at a posteromedial edge of the tibial bearing component to create a substantially continuous chamfer extending from the resected tibial surface to the medial articular surface of the tibial bearing component. Advantageously, this chamfer leaves an absence of material (i.e., a relief or void) at the posteromedial edge of the tibial prosthesis, thereby enabling deep flexion of the prosthesis without impingement between the tibial prosthesis and adjacent anatomic tissues or prosthetic structures.

To facilitate selection of proper prosthesis components, a set of trial tibial baseplate components are provided, with each component in the set sized to substantially cover various sizes of a proximal tibial surface exposed after resection. Each trial component has a perimeter that is substantially identical to the perimeter of correspondingly sized tibial baseplate, and is therefore larger than the corresponding tibial bearing component at the posteromedial portion owing to the void created by the posteromedial chamfer. The trial components include visual indicators of this posteromedial void, thereby establishing a visual acuity between the trial components and the final assembled tibial prosthesis. This visual acuity promotes surgeon confidence that the trial components are appropriately paired with their smaller counterpart permanent tibial bearing components.

In an alternative embodiment, the permanent tibial baseplate may be symmetrical or otherwise differently-shaped from the trial component. The asymmetric trial component may still be used to determine proper rotation, sizing, and orientation of the permanent component, as above, but may then be replaced with the differently-shaped tibial baseplate for final implantation. Where such a differently-shaped tibial baseplate is used, the trial component may include visual indication of the disparity between the trial periphery and the baseplate periphery. This visual indication of disparity promotes surgeon confidence in the final implanted position and orientation of the baseplate.

Proper rotational orientation of the baseplate and tibial bearing components is assessed by comparing one or more of the trial components to the natural resected tibial surface. To ensure that this rotational orientation is properly transferred to the permanent components, the trial components provide drill guide holes which can be used to locate and orient the proper location for one or more mounting holes for the permanent tibial baseplate. The corresponding tibial baseplate is then provided with fixation pegs formed at the same location relative to the baseplate periphery. Alternatively, the provisional component may include a central aperture corresponding to a stem or keel formed on the tibial baseplate.

In one form thereof, the present invention provides a tibial bearing component comprising: an inferior surface; an opposing superior surface defining a lateral articular surface and a medial articular surface; an anteroposterior axis disposed between the lateral articular surface and the medial articular surface and extending from an anterior edge to a posterior edge of the tibial bearing component; and a peripheral wall extending from the inferior surface to the superior surface, the peripheral wall having a tibial bearing chamfer extending from a posterior medial edge of the superior surface toward the inferior surface, the tibial bearing chamfer extending across at least 25% of an available proximal/distal distance between the superior and inferior surfaces at the posterior medial edge, the tibial bearing chamfer forming an acute bearing chamfer angle with the inferior surface such that the bearing chamfer extends proximally and anteriorly from the inferior surface toward the superior surface.

In another form thereof, the present invention provides a tibial prosthesis kit, the kit comprising: a tibial baseplate including medial and lateral compartments bounded by a baseplate periphery, the medial compartment including a posteromedial baseplate potion defining a baseplate chamfer, the baseplate chamfer defining an acute baseplate chamfer angle with respect to a coronal plane; a first tibial bearing component comprising: a first inferior surface sized to fit within the baseplate periphery; an opposing first superior surface; a first medial portion having a first medial articular surface forming part of the first superior surface; a first lateral portion disposed opposite the first medial portion with respect to an anteroposterior axis, the first lateral portion having a first lateral articular surface forming another part of the first superior surface; and a first bearing chamfer extending from a posterior medial edge of the first superior surface toward the first inferior surface, the first bearing chamfer extending across at least 25% of a first available proximal/distal distance between the first superior and first inferior surfaces at the posterior medial edge, the first bearing chamfer defining an acute first bearing angle with respect to the first inferior surface; and a second tibial bearing component comprising: a second inferior surface sized to fit within the baseplate periphery; an opposing second superior surface defining a second lateral articular surface and a second medial articular surface; and a second medial portion having a second medial articular surface forming part of the second superior surface; a second lateral portion disposed opposite the second medial portion with respect to an anteroposterior axis, the second lateral portion having a second lateral articular surface forming another part of the second superior surface; and a second bearing chamfer extending from a posterior medial edge of the second superior surface toward the second inferior surface, the second bearing chamfer extending across at least 25% of a second available proximal/distal distance between the second superior and second inferior surfaces at the posterior medial edge, the second bearing chamfer defining an acute second bearing angle with respect to the second inferior surface, the second bearing component differently sized from the first bearing component.

In yet another form thereof, the present invention provides a method of determining a tibial prosthesis size, the method comprising: providing a trial component having a void indicator; placing the trial component on a resected proximal tibial surface to create a buffer zone on all sides between a perimeter of the tibial surface and a perimeter of the trial component, the void indicator occupying a posteromedial area of the tibial surface when the trial component is placed on the tibial surface; removing the trial component; providing a tibial baseplate having a posteromedial baseplate chamfer; and implanting the tibial baseplate on the resected proximal tibia so that the baseplate chamfer occupies the posteromedial area.

In one aspect, the method further includes: providing a tibial bearing component having a posteromedial tibial bearing chamfer; and mounting the tibial bearing component on the tibial baseplate so that the tibial bearing chamfer and the baseplate chamfer form a substantially continuous chamfer.

In another aspect, the relief created by the chamfer prevents impingement of a femoral component, femur or soft tissues upon the tibial base plate chamfer in a deep flexion orientation corresponding to at least 155 degrees of flexion.

In still another form thereof, the present invention provides a family of tibial prostheses, the prostheses comprising: a plurality of trial components, each of the trial components comprising: a different size and geometrical arrangement defining a trial component perimeter, the geometrical arrangement including asymmetry about an anteroposterior axis; and a posteromedial area having a void indicator; a plurality of tibial baseplates having a bone-contacting surface and a superior surface, each of the bone-contacting surfaces defining a baseplate perimeter that is substantially identical to a respective one of the trial component perimeters; and a plurality of tibial bearing components, each of the tibial bearing components having a tibial bearing component perimeter that is substantially identical to a respective one of the trial components perimeters excluding the posteromedial area.

In one aspect, the anteroposterior axis is a home axis, the home axis defined as a line extending from a posterior point at the geometric center of an attachment area between a posterior cruciate ligament and the tibia, to an anterior point disposed on an anterior tubercle of the tibia, the tubercle having a tubercle width W, the anterior point disposed on the tubercle at a location medially spaced from a peak of the tubercle by an amount equal to W/6.

In another aspect, the void indicator comprises one of a contrasting color, contrasting texture, contrasting surface finish, and a geometric discrepancy.

In still another form thereof, the present invention provides a tibial prosthesis kit, the kit comprising: a tibial baseplate including a baseplate posteromedial portion with a baseplate chamfer formed thereon; a tibial bearing component including a tibial bearing posteromedial portion with a tibial bearing chamfer formed thereon, the tibial bearing component adapted to mount to the tibial baseplate to form a tibial prosthesis, the baseplate chamfer and the tibial bearing chamfer cooperating to define a gap between a posteromedial periphery the tibial baseplate and a corresponding posteromedial periphery the tibial bearing component when the tibial bearing component is attached to the tibial baseplate; and a plurality of trial components having means for identifying the gap.

In one aspect, the means for identifying the gap comprises one of a contrasting color, contrasting texture, contrasting surface finish, and a geometric discrepancy.

In still another form thereof, the present invention provides a tibial prosthesis kit, the kit comprising: a tibial baseplate defining a baseplate periphery, said tibial baseplate having a means for fixation to a bone; a trial component defining an asymmetric periphery different from said baseplate periphery, said trial component having at least one locator hole corresponding to the location of the means for fixation, said trial component having a void indicator indicating the location of portions of said asymmetric periphery not present in said baseplate periphery.

In still another form thereof, the present inventor provides a method of determining a tibial prosthesis size, the method comprising: providing a trial component defining a trial component periphery and having a void indicator within the trial component periphery; placing the trial component on a resected proximal tibial surface such that the void indicator occupies an area of the tibial surface when the trial component is placed on the tibial surface; removing the trial component; providing a tibial baseplate having a baseplate periphery that is different from said trial component periphery; and implanting the tibial baseplate on the resected proximal tibia so that the baseplate periphery occupies an area on the proximal tibia that corresponds to the trial component periphery with the void indicator removed.

BRIEF DESCRIPTION OF THE DRAWINGS

The above-mentioned and other features and advantages of this invention, and the manner of attaining them, will become more apparent and the invention itself will be better understood by reference to the following description of embodiments of the invention taken in conjunction with the accompanying drawings, wherein:

FIG. 3C is a coronal elevation, section view of another embodiment of the tibial prosthesis shown in FIG. 2A, taken along line 3C-3C;

FIG. 3D is an enlarged, partial view of the tibial prosthesis shown in FIG. 3C, illustrating a medial transition from an articular surface to a bearing periphery;

FIG. 4B is an enlarged, partial view of the tibial prosthesis shown in FIG. 4A, illustrating a posteromedial chamfer;

Corresponding reference characters indicate corresponding parts throughout the several views. The exemplifications set out herein illustrate exemplary embodiments of the invention, and such exemplifications are not to be construed as limiting the scope of the invention in any manner.

DETAILED DESCRIPTION

The present disclosure provides a knee joint prosthesis which permits a wide range of flexion motion, promotes desired prosthesis kinematics, protects natural soft tissue proximate the knee joint prosthesis, and facilitates proper rotational and spatial orientation and coverage of a tibial baseplate and tibial bearing component upon a resected proximal tibia.

As used herein, "proximal" refers to a direction generally toward the torso of a patient, and "distal" refers to the opposite direction of proximal, i.e., away from the torso of the patient. As used herein, "anterior" refers to a direction generally toward the front of a patient. "Posterior" refers to the opposite direction of anterior, i.e., toward the back of the patient.

For purposes of the present disclosure, a sagittal plane is a plane which extends distally and proximally, as well as anteriorly and posteriorly. For example, the plane of left/right symmetry in the human body is a sagittal plane. In the context of a prosthesis, such as prosthesis 10 described below, the plane that generally divides the prosthesis into medial and lateral halves is a sagittal plane, and may be inclusive of an anteroposterior axis such as home axis $A_H$ (described below).

For purposes of the present disclosure, a transverse plane is perpendicular to the sagittal plane, and extends medially and laterally as well as anteriorly and posteriorly. For example, a plane that separates the human torso from the legs is a transverse plane. In the context of a prosthesis, the bone-contacting surface (e.g., surface 35 shown in FIG. 1A and described below) and the corresponding proximal surface of a tibia after resection both define generally transverse planes. A coronal plane is perpendicular to the sagittal and transverse planes. For example, the plane separating the front and back sides of a human is a coronal plane.

Figure 2A:
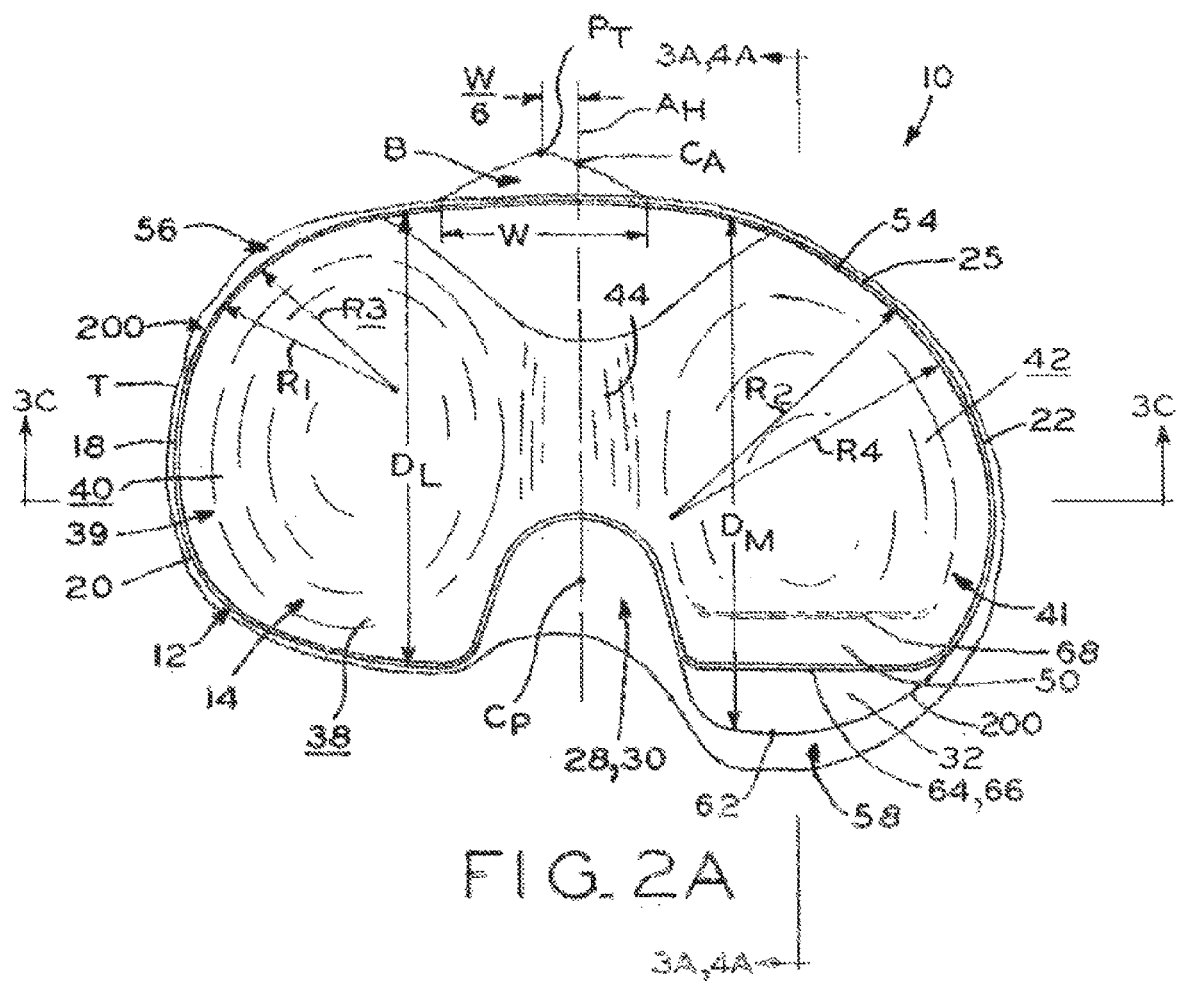
FIG. 2A is a top plan view of a resected proximal tibial surface, with a prosthetic tibial baseplate component and tibial bearing component of FIGS. 1A and 1B mounted thereon.

Referring to FIG. 2A, tibia T includes tibial tubercle B having mediolateral width W, with tubercle midpoint $P_T$ located on tubercle B approximately halfway across width W. While tubercle B is shown as having midpoint $P_T$ at the "peak" or point of maximum anterior eminence, it is recognized that midpoint $P_T$ of tibia T may be spaced from such a peak. Tibia T also includes attachment point $C_P$ representing the geometric center of the attachment area between the anatomic posterior cruciate ligament (PCL) and tibia T. Recognizing that the PCL typically attaches to a tibia in two ligament "bundles," one of which is relatively anterior, lateral and proximal and the other of which is relatively posterior, medial and distal, attachment point $C_P$ is contemplated as representing the anterior/lateral attachment area in an exemplary embodiment. However, it is contemplated that the posterior/medial attachment area, or the entire attachment area, could be used.

In the context of patient anatomy, "home axis" $A_H$ (FIG. 2A) refers to a generally anteroposterior axis extending from posterior point $C_P$ to an anterior point $C_A$, in which anterior point $C_A$ is disposed on tubercle B and medially spaced from tubercle midpoint $P_T$ by an amount equal to W/6. Stated another way, anterior point $C_A$ is laterally spaced by an amount equal to W/3 from the medial end of mediolateral width W, such that point $C_A$ lies on the "medial third" of the anterior tibial tubercle.

In the context of a prosthesis, such as tibial prosthesis 10 described below, "home axis" $A_H$ refers to an axis oriented with respect to baseplate 12 such that the baseplate home axis $A_H$ of baseplate 12 is aligned with home axis $A_H$ of tibia T after implantation of baseplate 12 in a proper rotational and spatial orientation. In the illustrative embodiment shown in FIG. 2B and described in detail below, home axis $A_H$ bisects PCL cutout 28 at the posterior portion of periphery 200 of tibial plate 18 (FIG. 2A), and bisects anterior edge 202 at the anterior edge of periphery 200 of tibial plate 18. It is contemplated that home axis $A_H$ may be oriented to other baseplate features, it being understood home axis $A_H$ of baseplate 12 is positioned such that that proper alignment and orientation of baseplate 12 upon tibia T positions home axis $A_H$ of baseplate 12 coincident with home axis $A_H$ of tibia T. Home axis $A_H$ of tibial baseplate 12 may be said to be an anteroposterior axis, as home axis $A_H$ extends generally anteriorly and posteriorly when baseplate 12 is implanted upon tibia T.

The embodiments shown and described in the Figures illustrate a left knee and associated features of a left-knee prosthesis. In an exemplary embodiment, an associated right knee configuration is a mirror image of the left-knee configuration about a sagittal plane. Thus, it will be appreciated that all aspects of the prosthesis described herein are equally applicable to a left- or right-knee prosthesis.

1. Tibial Prosthesis Construction.

Figure 1A:
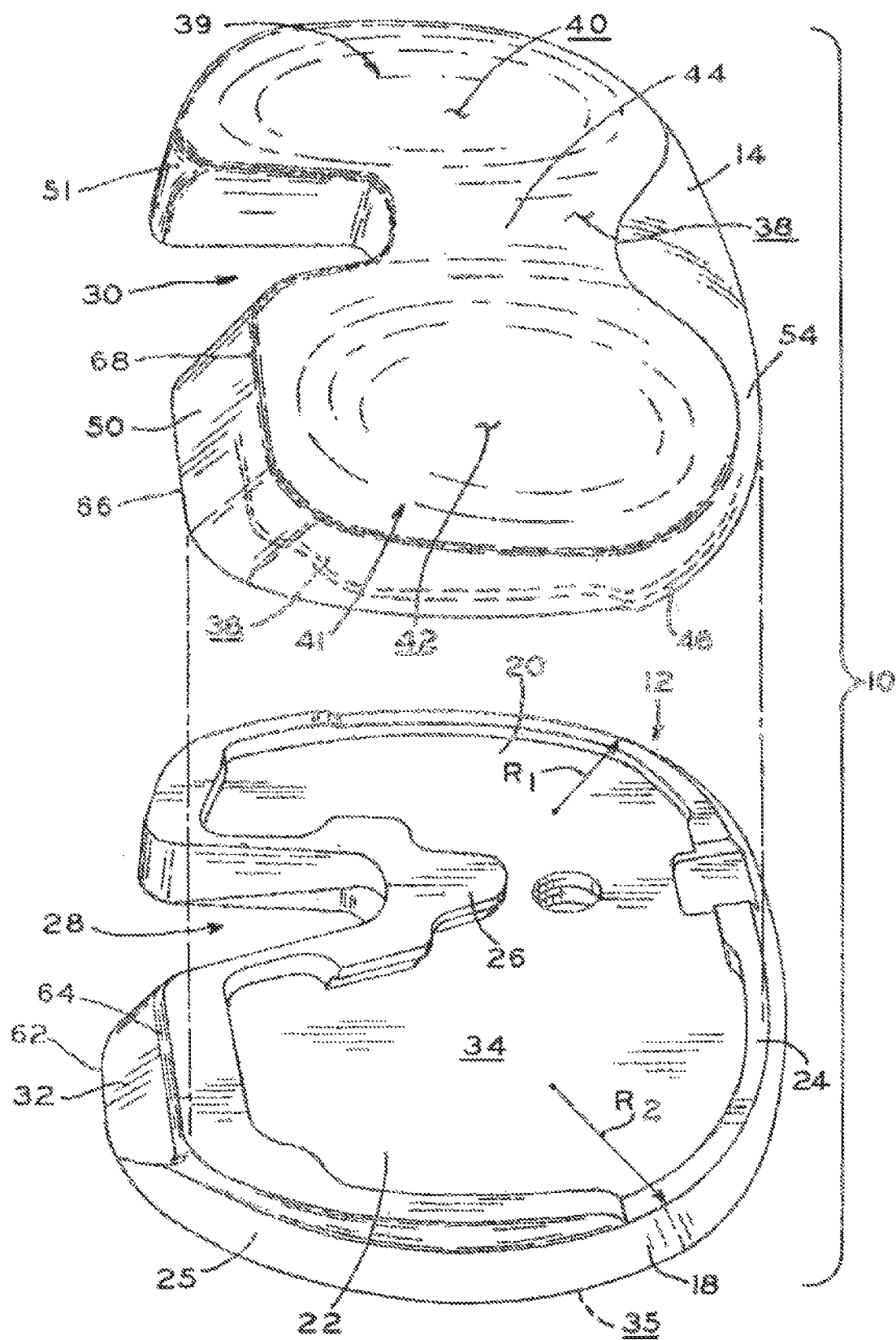
FIG. 1A is an exploded, perspective view of a tibial baseplate and tibial bearing component in accordance with the present disclosure.
Figure 1B:
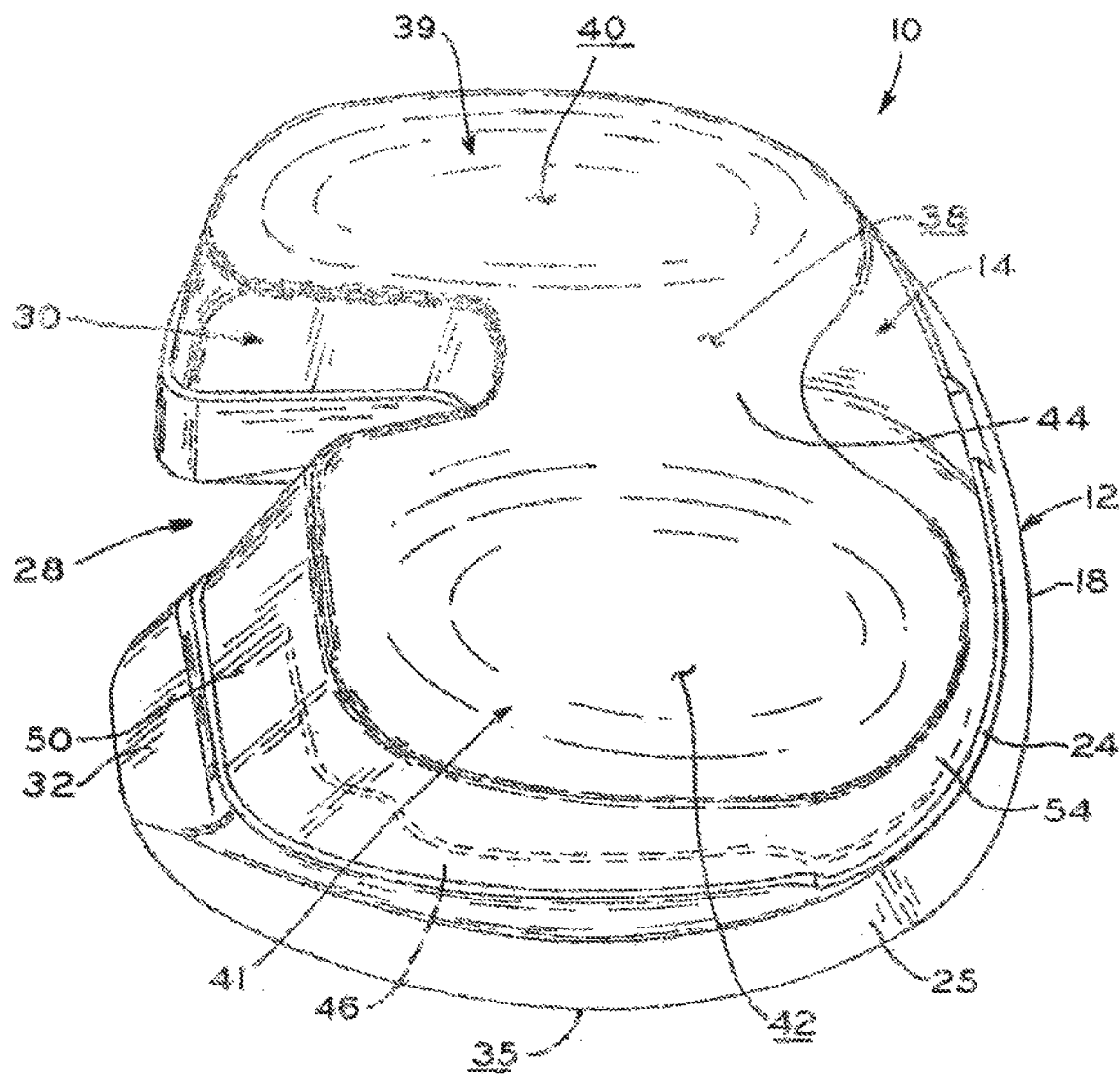
FIG. 1B is a perspective view of the tibial baseplate and tibial bearing component shown in FIG. 1A.

Referring now to FIGS. 1A and 1B, tibial prosthesis 10 includes tibial baseplate 12 and tibial bearing component 14. Tibial baseplate 12 may include a stem or keel 16 (see, e.g., FIGS. 3A, 3C and 4A) extending distally from a proximal tibial plate 18 for fixation of tibial baseplate to a tibia T. Alternatively, a plurality of fixation pegs (not shown) may be provided to affix tibial plate 18 to tibia T.

Figure 2B:
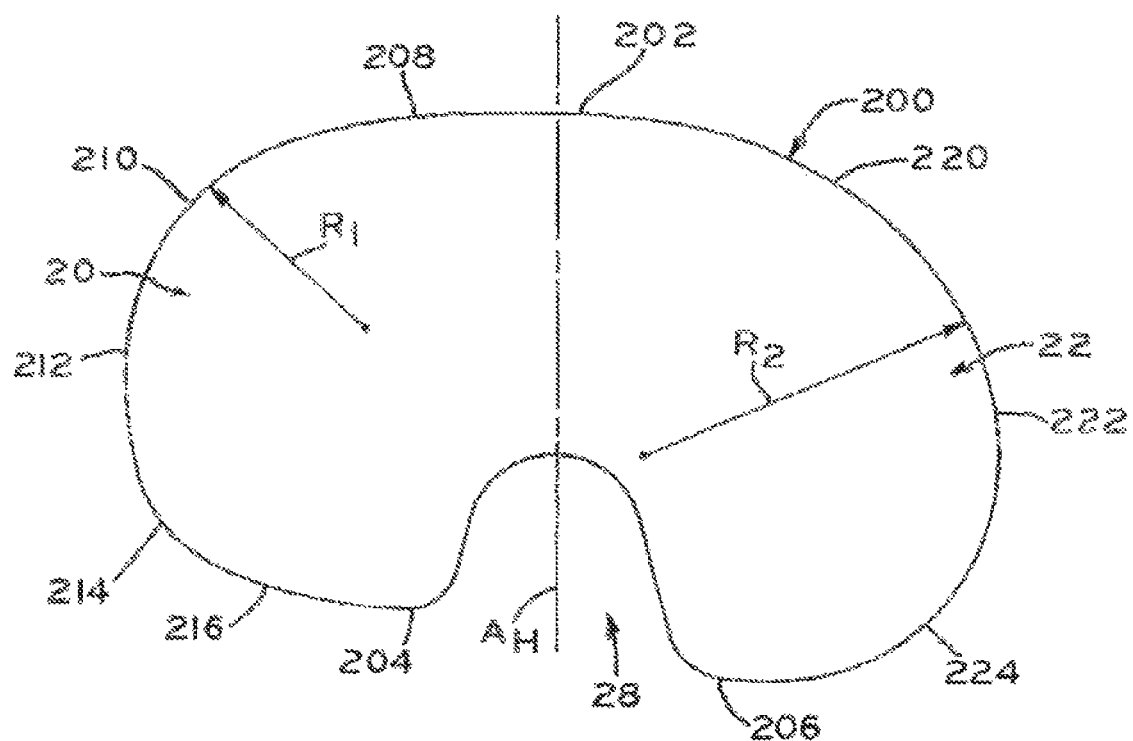
FIG. 2B is a schematic view of a periphery of the tibial baseplate component shown in FIG. 2A.

Referring now to FIGS. 1A and 2A, tibial baseplate 12 includes lateral condylar compartment 20 and medial condylar compartment 22 which form medial and lateral "halves" of tibial plate 18 divided by home axis $A_H$ (which extends between compartments 20, 22 as shown in FIG. 2B). However, lateral and medial condylar compartments 20, 22 are dissimilar in size and shape, rendering tibial plate 18 of tibial baseplate 12 asymmetrical about home axis $A_H$ such that medial compartment 22 actually represents more than half of the total area contained within periphery 200. Periphery 200 represents the outer limits, or bounds, of lateral and medial compartments 20, 22.

As shown in FIG. 2B, lateral condylar compartment 20 defines radius $R_1$ at anterolateral corner 210, and medial condylar compartment 22 defines radius $R_2$ at anteromedial corner 220. Anteromedial radius $R_2$ is substantially larger than anterolateral radius $R_1$, thereby imparting a relatively more "boxy" appearance to lateral condylar compartment 20, and a more "rounded" appearance to medial condylar compartment 22.

This asymmetry is specifically designed so that peripheral wall 25 traces the perimeter of the resected proximal surface of tibia T, such that tibial plate 18 covers a large proportion of the resected proximal tibial surface as shown in FIG. 2A. This substantial coverage encourages and facilitates proper rotational and spatial orientation of tibial baseplate 12 upon tibia T, and provides a large overall profile of baseplate 12 which creates sufficient space for large-radius, "soft-tissue friendly" edges as described in detail below. Exemplary asymmetric profiles for tibial baseplate 12 are described in U.S. patent application Ser. Nos. 13/189,336, 13/189,338 and 13/189,339, each filed on Jul. 22, 2011 and entitled ASYMMETRIC TIBIAL COMPONENTS FOR A KNEE PROSTHESIS, the entire disclosures of which are hereby expressly incorporated by reference herein.

As best seen in FIGS. 2A and 2B, lateral condylar compartment 20 of tibial plate 18 defines overall anteroposterior extent $D_L$ which is less than overall anteroposterior extent $D_M$ of medial condylar compartment 22. This disparity in anteroposterior extent arises from the additional posterior reach of medial condylar compartment 22 as compared to lateral condylar compartment 20. The additional posteromedial material of tibial plate 18 includes chamfer 32 (FIG. 1A) formed in peripheral wall 25, which forms angle α (FIG. 7) with bone-contacting surface 35 of tibial plate 18. As described in detail below, chamfer 32 forms part of a larger posteromedial chamfer that provides a relief space for soft tissues and bone in deep flexion of prosthesis 10.

Turning back to FIG. 1A, tibial bearing component 14 includes lateral portion 39, medial portion 41, inferior surface 36 adapted to couple to tibial baseplate 12, and superior surface 38 adapted to articulate with condyles of a femoral component (such as femoral component 60 shown in FIG. 7 and described in detail below). Superior surface 38 includes lateral articular surface 40 in lateral portion 39 and medial articular surface 42 in medial portion 41, with eminence 44 (FIG. 2A) disposed between articular surfaces 40, 42. Referring to FIG. 2A, eminence 44 is a gently elevated portion which generally corresponds in shape and size with a natural tibial eminence of tibia T prior to resection.

Tibial plate 18 of tibial baseplate 12 further includes a distal or bone contacting surface 35 and an opposing proximal or superior surface 34, with superior surface 34 having raised perimeter 24 and locking mechanism 26 formed between lateral and medial compartments 20, 22. Superior surface 34 is sized to mate with inferior surface 36 of tibial bearing component 14, such that inferior surface fits entirely within the periphery defined by superior surface 34 (i.e., bearing component 14 does not "overhang" tibial plate 18 at any point). Raised perimeter 24 and locking mechanism 26 cooperate to retain tibial bearing component 14 upon tibial baseplate 12. More particularly, inferior surface 36 of tibial bearing component 14 includes peripheral recess 46 sized and positioned to correspond with raised perimeter 24 of tibial plate 18. Inferior surface 36 may further include central recess 47 (see, e.g., FIG. 3C) disposed between lateral and medial articular surfaces 40, 42 which cooperates with locking mechanism 26 of tibial plate 18 to fix tibial bearing component 14 to tibial baseplate 12 in a desired position and orientation. However, it is contemplated that tibial bearing component 14 may be affixed to baseplate 12 by any suitable mechanism or method within the scope of the present disclosure, such as by adhesive, dovetail tongue/groove arrangements, snap-action mechanisms, and the like.

Exemplary tibial baseplate and tibial bearing component locking mechanisms are described in U.S. provisional patent application Ser. Nos. 61/367,374 and 61/367,375 filed Jul. 24, 2010, and U.S. patent application Ser. Nos. 13/189,324 and 13/189,328 filed Jul. 22, 2011, all entitled TIBIAL PROSTHESIS, the entire disclosures of which are hereby expressly incorporated herein by reference.

Turning to FIG. 2B, periphery 200 of tibial plate 18 surrounds lateral compartment 20 and medial compartment 22, each of which define a plurality of lateral and medial arcs extending between anterior edge 202 and lateral and medial posterior edges 204, 206 respectively. In the illustrative embodiment of FIG. 2B, anterior edge 202, lateral posterior edge 204 and medial posterior edge 206 are substantially planar and parallel for ease of reference. However, it is contemplated that edges 202, 204, 206 may take on other shapes and configurations within the scope of the present disclosure, such as angled or arcuate.

Generally speaking, a "corner" of periphery 200 may be said to be that portion of the periphery where a transition from an anterior or posterior edge to a lateral or medial edge occurs. For example, in the illustrative embodiment of FIG. 2B, the anterior-lateral corner is principally occupied by anterior-lateral corner arc 210, which defines a substantially medial-lateral tangent at the anterior end of arc 210 and a substantially anteroposterior tangent at the lateral end of arc 210. Similarly, the anterior-medial corner of periphery 200 is principally occupied by anterior-medial corner arc 220, which defines a substantially medial-lateral tangent at the anterior end of arc 220 and a more anteroposterior tangent at the lateral end of arc 220. Posterior-lateral arc 214 and posterior-medial arc 224 similarly define substantially medial-lateral tangents at their respective posterior ends and substantially anteroposterior tangents at the lateral and medial ends, respectively.

As shown in FIGS. 1B and 2A, the outer periphery of tibial bearing component 14 generally corresponds with the outer periphery 200 of tibial plate 18, except for the posteromedial extent of plate 18 as compared with tibial bearing component 14. The anterolateral "corner" of tibial bearing component 14 defines radius $R_3$ having a generally common center with radius $R_1$ of baseplate 12 in a transverse plane, i.e., radii $R_1$ and $R_3$ are substantially coincident in a plan view. Similarly, the anteromedial "corner" of tibial bearing component 14 defines radius $R_4$ having a generally common center with radius $R_2$ of baseplate 12 in a transverse plane, i.e., radii $R_2$ and $R_4$ are substantially coincident when in a plan view. $R_3$ defines a slightly smaller radial length as compared to $R_1$, and $R_4$ defines a slightly smaller radial length as compared to $R_2$, such that the anterior portion of perimeter wall 54 of tibial bearing component 14 is set back slightly from the anterior portion of peripheral wall 25 of tibial baseplate 12. As with the above-described comparison between radii $R_1$ and $R_2$, anteromedial radius $R_4$ is substantially larger than anterolateral radius $R_3$.

Medial portion 41 of tibial bearing component 14 may be biased anteriorly, such that the anterior-medial edges of tibial bearing component 14 and tibial plate 18 coincide as shown in FIG. 2A. This anterior bias leaves baseplate chamfer 32 fully exposed at the portion of tibial plate 18 corresponding to posterior-medial corner 224 and posterior edge 206 of periphery 200 (FIG. 2B). In contrast, lateral articular surface 40 substantially completely covers lateral compartment 20 of tibial plate 18, and is generally centered with respect to lateral compartment 20. In view of this anterior bias of medial portion 41, it may be said that tibial bearing component 14 is asymmetrically oriented upon tibial plate 18 such that medial portion 41 appears to have been rotated forward. In addition to ensuring exposure of baseplate chamfer 32, this asymmetric mounting of tibial bearing component 14 upon tibial plate 18 ensures a desired articular interaction between tibial prosthesis 10 and femoral component 60, as described in detail below.

In the illustrated embodiment, tibial plate 18 includes cutout 28 (FIG. 1A) disposed between condylar compartments 20, 22 to leave PCL attachment point $C_P$ (FIG. 2A) accessible and allow the PCL to pass therethrough. Tibial bearing component 14 similarly includes cutout 30 (FIG. 1A). Thus, tibial prosthesis 10 is adapted for a cruciate retaining (CR) surgical procedure, in which the posterior cruciate ligament is not resected during implantation of tibial prosthesis 10. However, it is contemplated that a prosthesis in accordance with the present disclosure may be made for "posterior stabilized" (PS) or "ultracongruent" (UC) designs in which the posterior cruciate ligament is resected during surgery. Thus, PCL cutouts 28, 30 may be optionally omitted for prostheses which do not retain the anatomic PCL. One illustrative PS design, shown in FIG. 3C, includes proximally extending spine 45 monolithically formed with tibial bearing component 14C. Spine 45 is designed to interact with a corresponding cam (not shown) of a femoral component (e.g., femoral component 60 shown in FIG. 7).

In an alternative embodiment, tibial baseplate 12 may be omitted such that tibial prosthesis 10 is formed solely from tibial bearing component 14. Tibial bearing component 14 may have a stem or keel (not shown) similar to keel 16 of baseplate 10, or may have fixation pegs for fixation to tibia T. Tibial bearing component 14 may therefore have lateral and medial portions 39, 41 and a distal fixation structure which are monolithically formed of a single material, such as polyethylene or another suitable polymer. Alternatively, lateral and medial portions 39, 41 may be made of a different, but integrally formed material as compared to the distal fixation structure.

Advantageously, the relatively large area of bone-contacting surface 35 of tibial plate 18 facilitates a large amount of bone ingrowth where bone ingrowth material is provided in tibial baseplate 12. For example, baseplate 12 may be at least partially coated with a highly porous biomaterial to facilitate firm fixation thereof to tibia T. A highly porous biomaterial is useful as a bone substitute and as cell and tissue receptive material. A highly porous biomaterial may have a porosity as low as 55%, 65%, or 75% or as high as 80%, 85%, or 90%. An example of such a material is produced using Trabecular Metal™ Technology generally available from Zimmer, Inc., of Warsaw, Ind. Trabecular Metal™ is a trademark of Zimmer, Inc. Such a material may be formed from a reticulated vitreous carbon foam substrate which is infiltrated and coated with a biocompatible metal, such as tantalum, by a chemical vapor deposition ("CVD") process in the manner disclosed in detail in U.S. Pat. No. 5,282,861 to Kaplan, the entire disclosure of which is expressly incorporated herein by reference. In addition to tantalum, other metals such as niobium, or alloys of tantalum and niobium with one another or with other metals may also be used.

Generally, the porous tantalum structure includes a large plurality of struts (sometimes referred to as ligaments) defining open spaces therebetween, with each strut generally including a carbon core covered by a thin film of metal such as tantalum, for example. The open spaces between the struts form a matrix of continuous channels having no dead ends, such that growth of cancellous bone through the porous tantalum structure is uninhibited. The porous tantalum may include up to 75%, 85%, or more void space therein. Thus, porous tantalum is a lightweight, strong porous structure which is substantially uniform and consistent in composition, and closely resembles the structure of natural cancellous bone, thereby providing a matrix into which cancellous bone may grow to provide fixation of implant 10 to the patient's bone.

The porous tantalum structure may be made in a variety of densities in order to selectively tailor the structure for particular applications. In particular, as discussed in the above-incorporated U.S. Pat. No. 5,282,861 the porous tantalum may be fabricated to virtually any desired porosity and pore size, and can thus be matched with the surrounding natural bone in order to provide an improved matrix for bone ingrowth and mineralization.

2. Soft Tissue Impact Reduction and Deep Flexion Enablement.

Tibial bearing component 14 advantageously reduces the potential impact of prosthesis 10 on the adjacent anatomic soft tissues of a knee after implantation, even when the prosthesis is articulated into deep flexion in vivo. This reduced impact results from features included in bearing component 14, and such features are facilitated by the size, shape and configuration of tibial baseplate 12.

Figure 7:
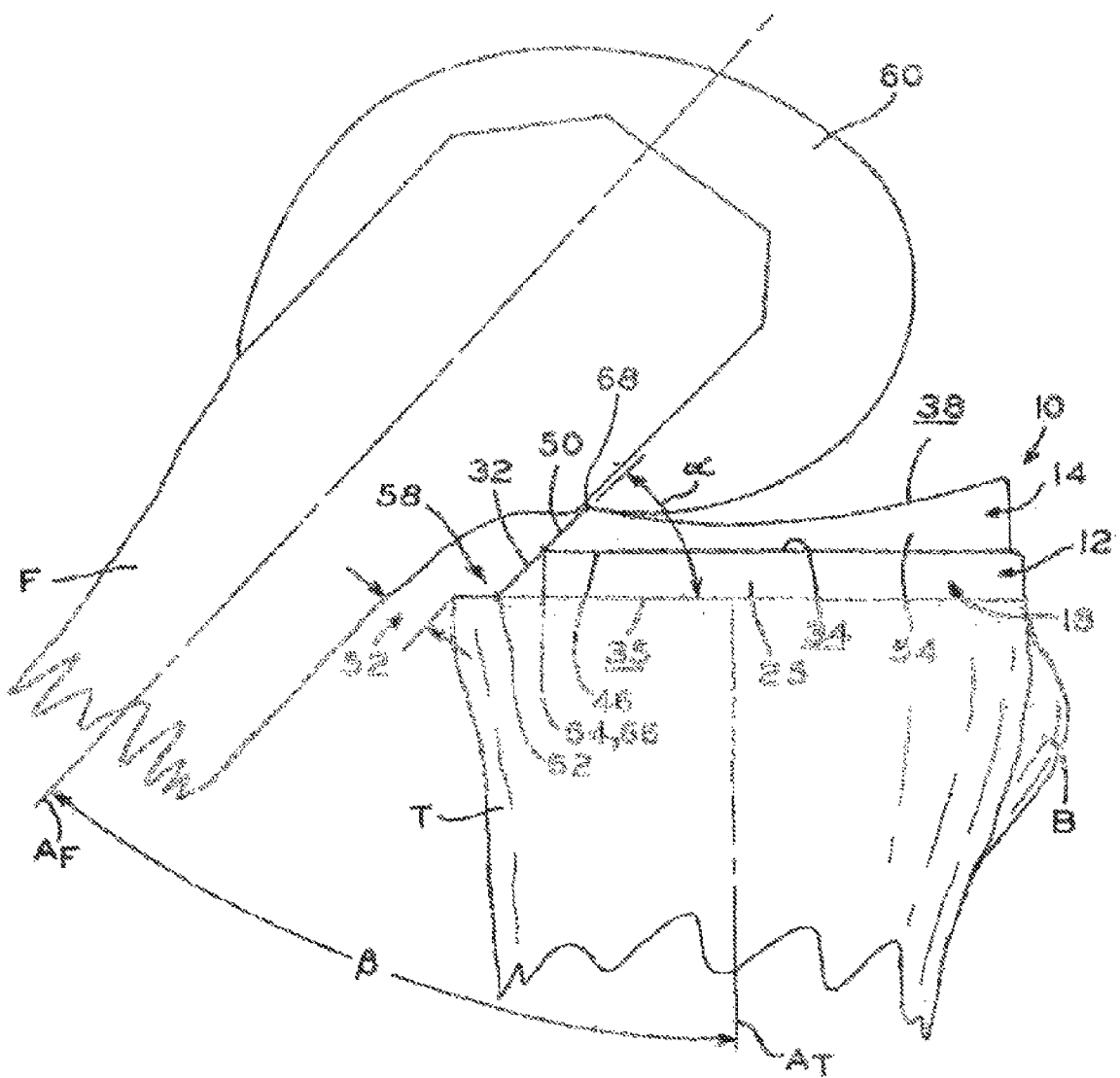
FIG. 7 is a side, elevation view of the tibia and prosthetic components shown in FIG. 4.

One feature which reduces soft tissue impact potential is baseplate chamfer 32, which cooperates with bearing chamfer 50 to create relief 52 (FIG. 7). As noted above and shown in FIG. 2A, the otherwise close match between peripheral wall 54 of tibial bearing 14 and peripheral wall 25 of tibial baseplate 12 deviates around posteromedial corner 224 and posterior edge 206 of medial compartment 22 (see, e.g., FIGS. 2A and 2B). In this shift from congruence to incongruence, medial compartment 22 of tibial plate 18 extends posteriorly to cover a substantial portion of the proximal resected surface of tibia T (FIGS. 2A and 7), while medial portion 41 of tibial bearing component 14 only extends posteriorly as far as the anterior end of chamfer 32. Thus, as illustrated in FIG. 7, tibial bearing component 14 does not "overhang" chamfer 32.

As best seen in FIGS. 1A and 7, baseplate chamfer 32 extends proximally and anteriorly from a posterior/distal edge 62, corresponding to posterior edge 206 of periphery 200 shown in FIG. 2B, to an anterior/proximal edge 64 of chamfer 32. Similarly, bearing chamfer 50 extends proximally and anteriorly from posterior/distal edge 66, which is coincident with inferior surface 36 of bearing component 14, to an anterior/proximal edge 68 at the boundary of medial articular surface 42. When tibial bearing component 14 is assembled to tibial baseplate 12 as shown in FIGS. 1B and 7, medial portion 41 of tibial bearing component 14 (described above) is positioned to substantially align chamfers 32, 50. When so aligned, posterior/distal edge 66 of bearing chamfer 50 is disposed near anterior/proximal edge 64 of baseplate chamfer 32, such that chamfers 32, 50 cooperate to define a substantially continuous chamfer extending from the resected surface of tibia T to medial articular surface 42. However, as noted below, it is also contemplated that tibial and baseplate chamfers can cooperate to define a discontinuous chamfer within the scope of the present disclosure Chamfers 32, 50 cooperate to define relief 52 (FIG. 7) formed between femur F and tibial plate 18 when tibial prosthesis 10 is in a deep flexion orientation. In the illustrated embodiment of FIG. 7, the deep flexion orientation is defined by angle β between anatomic tibia axis $A_T$ and anatomic femoral axis $A_F$ of up to about 25 degrees to about 40 degrees, for example (i.e., about 140 degrees to 155 degrees of flexion or more).

Although asymmetric periphery 200 is designed to closely match an anatomic resected tibial surface as described above, certain aspects of periphery 200 are designed to intentionally deviate from the calculated anatomical shape to confer particular advantages with regard to minimization of soft tissue impact and the associated implanted knee prosthesis. Referring to FIG. 2A, for example, posterior edge 206 (FIG. 2B) of medial compartment 22 may be "pulled back" from the adjacent posterior-medial edge of tibia T to define void 58. In an exemplary embodiment, void 58 is created by leaving about 4 mm (measured as an anteroposterior extent) of the proximal resected surface of tibia T exposed. However, it is contemplated that void 58 may be smaller, or may be nonexistent. For some patient anatomies, for example, it may be possible to maximize tibial coverage by eliminating void 58 entirely (i.e., by positioning posterior edge 206 of medial compartment flush with the corresponding edge of tibia T). A surgeon may choose to eliminate gap 58 when presented with the opportunity to do so, provided other portions of periphery 200 do not extend beyond the periphery of the resected proximal surface of tibia T.

As illustrated in FIG. 7, void 58 cooperates with chamfers 32, 50 to create extra space for adjacent soft tissues and bone, particularly when prosthesis 10 is in a deep flexion configuration as illustrated. Advantageously, relief 52 between femur F and tibia T, made possible by chamfers 32, 50 as described above, cooperates with the "pulled back" or incongruent posterior medial void 58 to allow the deep flexion orientation to be achieved without allowing soft tissues to become trapped and impinged between femoral component 60/femur F and tibial plate 18/tibial bearing component 14. In deep flexion, soft tissues in the region of relief 52 can shift slightly into void 58 between femur F and tibia T within minimal resistance, thereby mitigating soft-tissue impacts by decreasing the likelihood of, e.g., compression or impingement with surrounding components. Moreover, any contact that may occur between a prosthesis made in accordance with the present disclosure and adjacent soft tissues will occur against the flat and broadly rounded surfaces of the prosthesis, such the impact of such contact on the tissue is minimized. To this end, it is contemplated that the specific geometry of chamfers 32, 50 may be modified for individual patient needs, such as to accommodate abnormally positioned and/or sized adjacent soft tissues.

In the illustrated embodiment of FIG. 7, bearing chamfer 50 defines a substantially linear profile in a sagittal plane. Where this linear profile extends across the medial/lateral extent of chamfers 32, 50, chamfers 32, 50 will also be generally coplanar, as illustrated. Chamfers define angle α with a transverse plane, e.g., with superior surface 34, bone contacting surface 35 and/or inferior surface 36 (which all lie in a generally transverse plane in the illustrated embodiment). Angle α is an acute angle that may have a value as little as about 35 degrees or 50 degrees and as large as about 55 degrees, 61 degrees, 70 degrees or 75 degrees, or within any range defined by any of the foregoing values.

Lateral chamfer 51 (FIG. 1A) may also be provided in order to facilitate a smooth transition from lateral articular surface 40 to the interface between inferior surface 36 of tibial bearing component 14 and superior surface 34 of tibial baseplate 12. Because lateral compartment 20 of periphery 200 (FIGS. 2A and 2B) provides maximum coverage of the resected proximal surface of tibia T, not all of the substantially conforming lateral portion 39 of tibial bearing 14 is needed to form lateral articular surface 40. Lateral chamfer 51 occupies the marginal space near articular surface 40, which is not normally used in articulation of prosthesis 10 with femoral component 60 (FIG. 7).

Advantageously, the smooth, rounded transition provided by lateral chamfer 51 provides clearance for bone and tissue during flexion. If an adjacent soft tissue does come into contact with lateral chamfer 51, the tension arising from such contact will be lower as compared to a prosthesis lacking such chamfer. Moreover, as with the other chamfers and rounded profiles provided on prosthesis 10, the rounded transition of lateral chamfer 51 minimizes the impact caused by any contact which may occur between chamfer 51 and adjacent soft tissues. At the same time, the buildup of material around lateral chamfer 51 provides posterior constraint to femoral component 60 (FIG. 7) and strengthens the posterior portion of lateral portion 39 of bearing component 14.

It is contemplated that bearing chamfer 50 may have an arcuate profile in a sagittal, coronal and/or transverse plane, and may include convex or concave curvature as required or desired for a particular application. For example, bearing component 14A shown in FIG. 3A is similar to bearing component 14 described above, and reference numbers in FIGS. 3A and 3B refer to analogous structures shown in FIGS. 1A and 2A and described above with respect to bearing component 14. However, chamfer 50A defines a slight curve in a sagittal plane as chamfer 50A extends from anterior/proximal edge 68A toward posterior/distal edge 66A of tibial bearing component 14A. For purposes of evaluating angle α (FIG. 7) in the context of curved chamfer 50A, a sagittal tangent line drawn at anterior/proximal edge 68A and compared to a coronal plane as described above. In the exemplary illustrated embodiment, angle α is about 61 degrees.

In the context of chamfers, e.g. chamfers 32, 50 and 50A, chamfer edges are referred to herein as "anterior/proximal" and "posterior/distal." These references refer to the relative positions of the chamfer edges in the context of the chamfers themselves, in the context of the position and orientation of the tibial prosthesis after implantation. Thus, an "anterior/proximal" edge is located at or near the anterior and proximal terminus of the chamfer, while a "posterior/proximal" edge located at or near the posterior and distal terminus of the chamfer (i.e., at the opposite end of the chamfer).

Figure 3A:
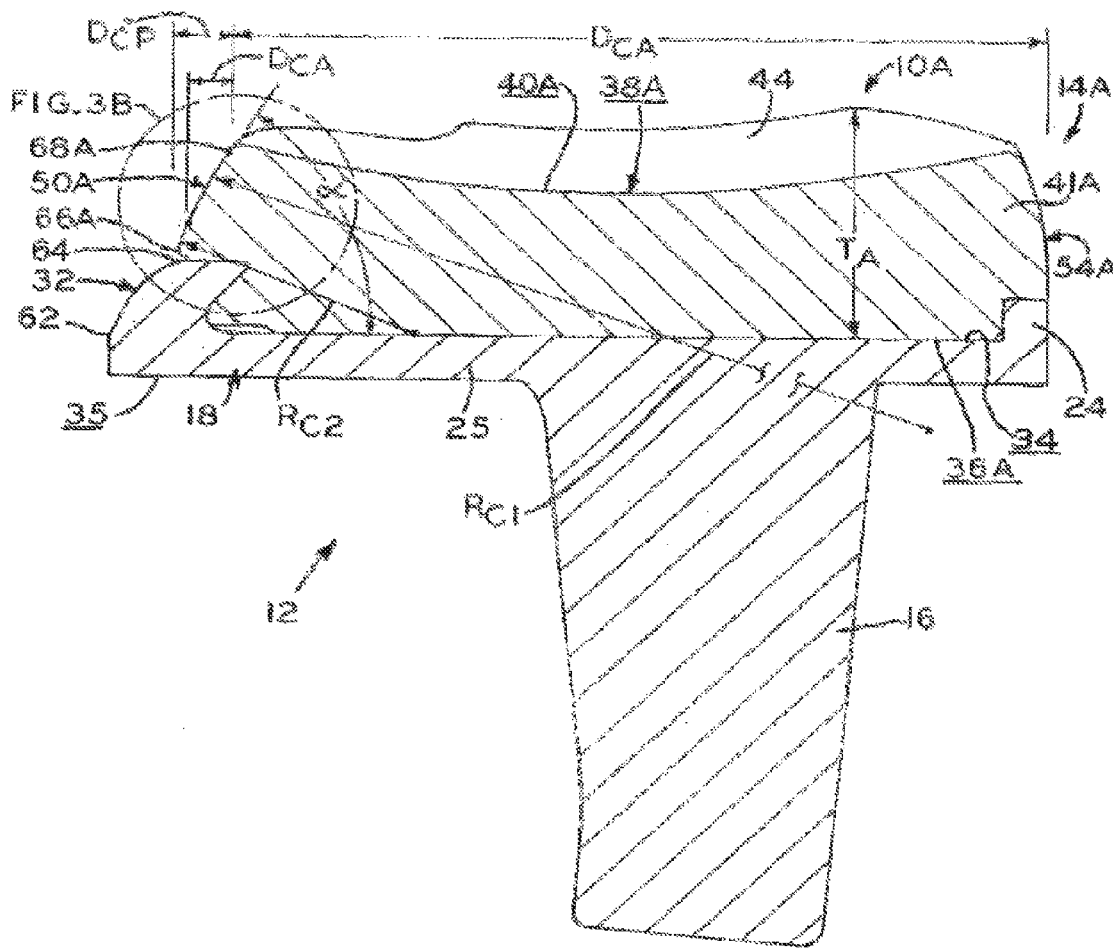
FIG. 3A is a sagittal elevation, section view of one embodiment of the tibial prosthesis shown in FIG. 2A, taken along line 3A-3A.
Figure 3B:
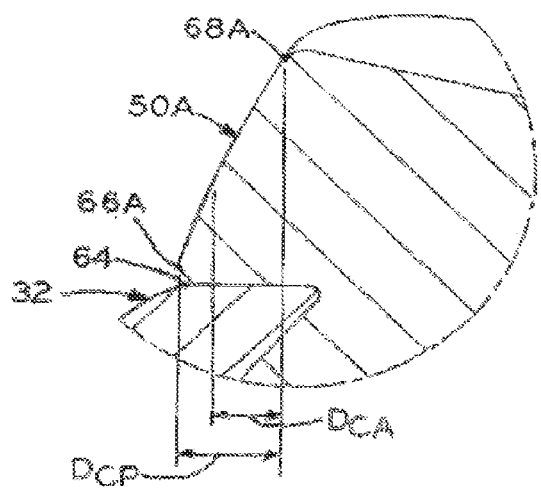
FIG. 3B is an enlarged, partial view of the tibial prosthesis shown in FIG. 3A, illustrating a posteromedial chamfer.

In the illustrative embodiment of FIG. 3A, chamfer 50A spans substantially the entire available proximal/distal distance, i.e., from superior surface 38A to anterior/proximal edge 64 of baseplate chamfer 32. However, it is contemplated that a chamfer in accordance with the present disclosure may extend across only a part proximal/distal distance, beginning near superior surface 38A but ending at a location proximal of the junction between the tibial plate (e.g., plate 18) and the tibial bearing component (e.g., component 14). After "early" terminus of the chamfer, the remainder of the vertical distance may be taken up by a vertical section of the bearing component periphery.

For example, chamfer 50A may extend as little as 25% or 32% of the total available proximal/distal distance, or as much as 100% of the total available proximal/distal distance, or may span and percentage distance within any range defined by any of the foregoing values. Moreover, it is contemplated that the configuration of chamfer 50A may vary depending on the configuration of tibial bearing component 14A. Where bearing component 14A is relatively thin, such as about 9-10 mm, for example, chamfer 50A may extend across a relatively larger proportion of the total available proximal/distal distance.

In some instances, bearing component 14A may be made thicker to accommodate additional resection of tibia T. For example, one such thicker bearing component is illustrated as component 14B, shown FIG. 4A and discussed below. In these instances, a similar chamfer to chamfer 50A may be provided in the proximal 9-10 mm of the available proximal/distal distance, while the remainder of such distance may be substantially vertical. This chamfer configuration retains the advantages provided by chamfer 50A, such as avoidance of soft tissue and bone impingement in deep flexion. Thus, in a relatively thicker component, a relatively smaller proportion of the total available proximal/distal distance may be needed to create a chamfer which provides the benefits described herein. In an exemplary embodiment, tibial bearing component may be provided as a kit of increasing thicknesses, with each thickness growing incrementally larger by 0.5 mm-1.0 mm. It is contemplated that such incremental growth in thickness may be larger, such as 2 mm, 3 mm or 4 mm for example.

In some other instances, the distal bone stock of femur F (FIG. 7) is significantly resected and tibial bearing component 14A is made thicker to accommodate the resulting proximal/distal joint space occupied by prosthesis 10. In these instances, a large proportion of the thicker bearing component may be given over to chamfer 50A, such that chamfer 50A extends across a large proportion of the available proximal/distal distance. This extensive chamfer 50A will advantageously minimize the chances for impingement of the adjacent soft tissues and bone.

The slight sagittal curve of chamfer 50A (described above) defines a sagittal chamfer radius $R_{C1}$ (FIG. 3A) which may be between as little as 5 mm or 65 mm and as much as 75 mm or 180 mm, or may be any value within any range defined by any of the foregoing values. Radius $R_{C1}$ extends across an anteroposterior extent $D_{CA}$ of about 2.0 mm, such that the length of the arc defined by radius $R_{C1}$ is about 4 mm where angle α is 61 degrees (as noted above). However, it is contemplated that anteroposterior extent $D_{CA}$ may be between about 0.5 mm and about 10.0 mm, and the arc length may vary accordingly.

A second radius, shown as radius $R_{C2}$ in FIG. 3A, is tangent to the posterior/distal end of radius $R_{C1}$ and spans the remaining distance to posterior/distal edge 66A to complete chamfer 50A. Radius $R_{C2}$ is smaller than radius $R_{C1}$, and may have a value as little as 5 mm or 12.5 mm and as much as 12.8 mm or 180 mm, or may be any value within any range defined by any of the foregoing values. Radius $R_{C1}$ cooperates with radius $R_{C2}$ to span the entire anteroposterior extent $D_{CP}$ of chamfer 50A, which extends from anterior/proximal edge 68A to posterior/distal edge 66A of bearing chamfer 50A as noted above. Anteroposterior extent $D_{CP}$ ranges from about 0.5 mm to about 10.0 mm. In the illustrated exemplary embodiment of FIG. 3B, anteroposterior extent $D_{CP}$ is about 2.7 mm. Thus, in the illustrated embodiment, the anteroposterior extent of radius $R_{C2}$ is about 0.7 mm.

The particular arrangement of chamfer 50A, as described above, has been found to represent an excellent balance between competing interests. On one hand, soft-tissue clearance is maximized by decreasing angle α, which increases the volume available in void 58. On the other hand, the additional material afforded by increasing angle α at the posteromedial portion of bearing component serves as a strengthening buttress, thereby providing a more robust bearing component. Chamfer 50A represents a strong component geometry that also provides enough space for natural soft tissues across a wide range of expected anatomical variability among patients.

However, it is contemplated that other chamfer profiles may be utilized within the scope of the present disclosure. Such profiles may include, for example, multiple linear sections cooperating to approximate a rounded profile, a pair of linear sections, or a concave rounded profile. Moreover, it is contemplated that patient-specific chamfer profiles may be created to match the anatomies of individual patients. For a patient-specific design, the posteromedial chamfer may be designed to correspond to the sagittal profile of the portion of the femur which is adjacent the posteromedial chamfer in deep flexion of the knee.

In an exemplary embodiment, a kit of prostheses may be provided with bearing components that all share common geometrical features of chamfer 50A. Referring to FIG. 3A, for example, bearing component 14A defines distance $D_C$ from the anterior edge thereof to anterior/proximal edge 68A of bearing chamfer 50A. In a kit of different prosthesis sizes designed to accommodate patients having various bone sizes, distance $D_C$ may vary widely. For example, distance $D_C$ may be as little as 20 mm, 25 mm or 36 mm for small prosthesis sizes, and as much as 56 mm, 65 mm, or 75 mm for large prosthesis sizes, or may be any value within any range defined by any of the foregoing values.

Despite this substantial variability, exemplary bearing components (including component 14A) can utilize a common angle α, anteroposterior extent $D_{CA}$ of the proximal/anterior portion of the chamfer, and overall chamfer anteroposterior extent $D_{CP}$ as described above. However, it is contemplated that radii $R_{C1}$, $R_{C2}$ may vary across prosthesis sizes, such as within the ranges set forth above, in order to ensure smooth and "soft-tissue friendly" transitions from the medial articular surface (e.g., surface 42) to the chamfer (e.g., chamfer 50A).

Figure 4A:
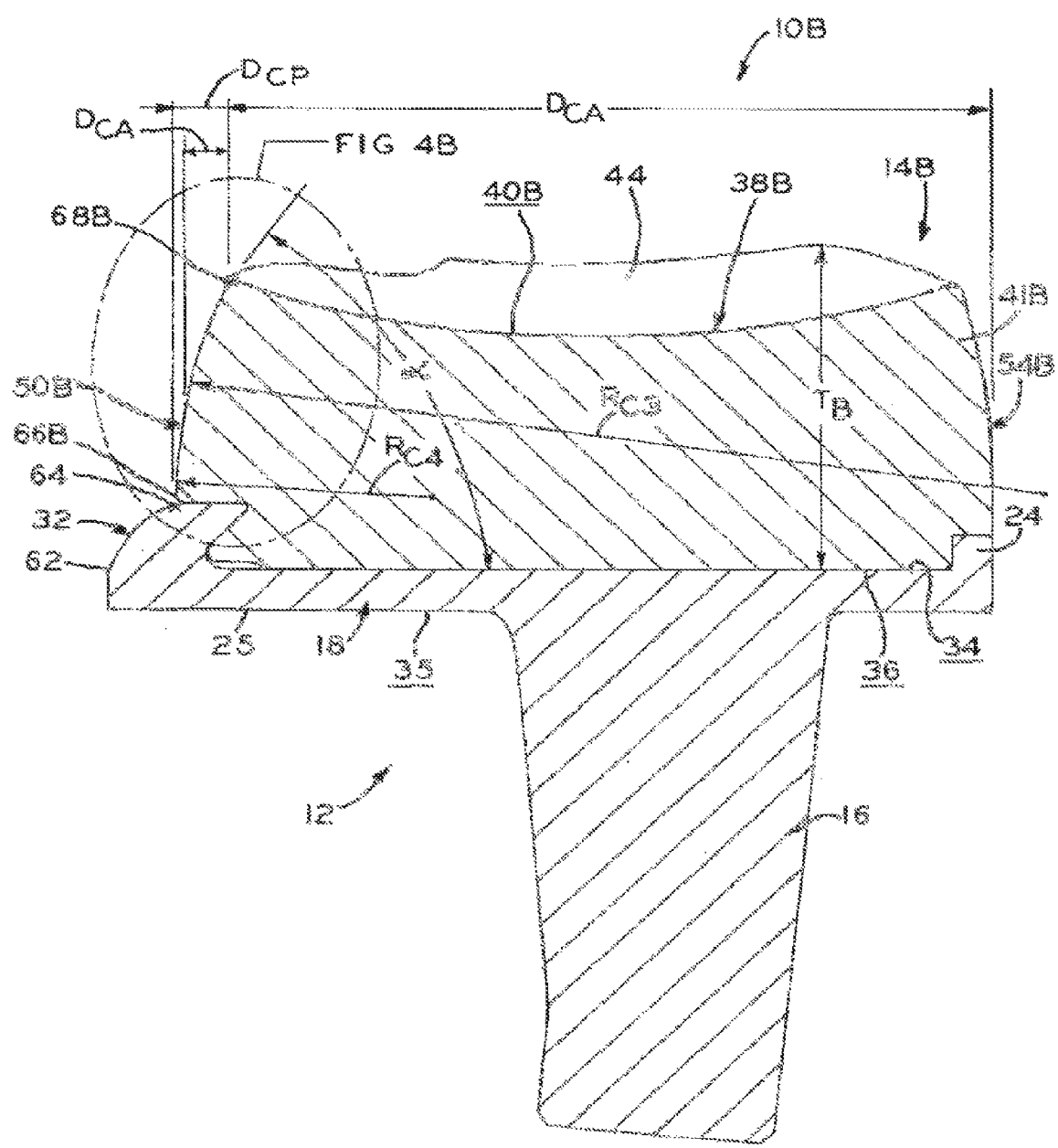
FIG. 4A is a sagittal elevation, section view of another embodiment of the tibial prosthesis shown in FIG. 2A, taken along line 4A-4A.

Turning to FIGS. 4A and 4B, prosthesis 10B including a thickened tibial bearing component 14B is shown. Bearing component 14B shown in FIG. 4A is similar to bearing component 14A described above, and reference numbers in FIGS. 4A and 4B refer to analogous structures shown in FIGS. 3A and 3B and described above with respect to bearing component 14A. However, bearing component 14B defines overall thickness $T_B$ which is substantially larger than the corresponding overall thickness $T_A$ of bearing component 14A. Bearing component 14B defines the same overall anteroposterior extent as bearing component 14A (i.e., distance $D_C$ plus distance $D_{CP}$), and may be used interchangeably with bearing component 14A to effectively increase the overall thickness of prosthesis 10. Such increased thickness may be used to accommodate a more extensive resection of tibia T, as noted above, or to accommodate the ligament configuration of a particular patient, for example.

Thickened bearing component 14B includes bearing chamfer 50B, which spans substantially the entire distance in a sagittal plane, as shown, from anterior/proximal edge 68B to posterior/distal edge 66B. Despite this additional proximal/distal span of chamfer 50B as compared to chamfer 50A, anteroposterior extents $D_{CA}$ and $D_{CP}$ remain unchanged, i.e., at about 2.0 mm and about 2.7 mm respectively. Angle α, again taken from a tangent to the arcuate sagittal profile of the proximal portion of chamfer 50B, also remains unchanged.

Radius $R_{C3}$, which remains the radius value for chamfer 50B across the anteroposterior extent $D_{CA}$ in a similar fashion to Radius $R_{C1}$ discussed above, is larger than radius $R_{C4}$ which extends across the remainder of overall anteroposterior extent $D_{CP}$ in similar fashion to radius $R_{C2}$. However, the nominal values of radii $R_{C3}$, $R_{C4}$ may be different from radii $R_{C1}$, $R_{C2}$ respectively. In an exemplary embodiment, for example, radius $R_{C3}$ may have a value as little as 55 mm or 65 mm and as much as 75 mm or 180 mm, or may be any value within any range defined by any of the foregoing values. Radius $R_{C4}$ may have a value as little as 5 mm or 12.5 mm and as much as 12.8 mm or 180 mm, or may be any value within any range defined by any of the foregoing values.

Advantageously, chamfer 50B defines a chamfer profile that is substantially the same as chamfer 50A near anterior/proximal edge 68B, thereby preventing impingement of femur F and/or adjacent soft tissues in a similar manner to chamfer 50A. Meanwhile, the reduction in radius $R_{C3}$ as compared to radius $R_{C1}$, imparts an overall "steeper" sagittal profile to chamfer 50B as compared to chamfer 50A. This steeper profile provides additional posterior buttressing of medial portion 41A, while the additional thickness $T_B$ provides for ample volume in void 58 for soft tissue clearance.

In addition to the posteromedial features discussed above, additional soft-tissue impact reduction may be achieved at the medial and lateral edges of bearing component 14. The relatively large size of tibial plate 18 (covering a large proportion of the resected proximal surface of tibia T) cooperates with the close congruence of tibial bearing component 14 thereto to enable a relatively large superior surface 38 of tibial bearing component 14. Because not all of this large superior surface area 38 is needed for lateral and medial articular surfaces 40, 42 (FIG. 2A), tibial bearing component 14 provides sufficient non-articular surface area around the periphery of lateral and medial articular surfaces 40, 42 to allow for "pulled back" areas and relatively large-radius, rounded transitions between such articular surfaces and peripheral wall 54 of tibial bearing component 14. These features minimize or prevent friction between tibial prosthesis 10 and any surrounding soft tissues, such as the iliotibial (IT) band, which may remain in place after implantation of prosthesis 10.

Similar to the "pulled back" portion of periphery 200 in the posteromedial portion at posterior-medial corner 224 and posterior edge 206, described in detail above, tibial baseplate 12 and tibial bearing component 14 each have anterior-lateral corners which are intentionally "pulled back" from an expected periphery of tibia T to create gap 56 (FIG. 2A) between the anterior-lateral area of the resected surface of tibia T and prosthesis 10. Advantageously, gap 56 moves the anterior-lateral corners of baseplate 12 and tibial bearing component 14 away from the area typically occupied by the iliotibial band, thereby minimizing the potential for impingement of the IT band upon prosthesis 10. In an exemplary embodiment, gap 56 may range from 0.5 mm for a small-size prosthesis, to 1 mm for a medium-sized prosthesis, to 2 mm for a large-sized prosthesis.

For certain patients or in certain ranges of prosthesis articulation, however, the human iliotibial (IT) band may touch the anterolateral corner of prosthesis 10. In some instances, the medial collateral ligament (MCL) may also touch the medial edge of prosthesis 10. As noted above, the large available surface area afforded by asymmetric periphery 200 of tibial baseplate 12 also affords ample space for peripheral transitions from superior surface 38 to peripheral wall 54 of tibial bearing component 14.

Turning to FIGS. 3C and 3D, transition radii $R_{TL}$, $R_{TM}$ are illustrated as the radii formed by the transition between lateral and medial articular surfaces 40, 42 and lateral and medial edges 72, 74 of peripheral wall 54 respectively. As best seen in FIG. 3D with respect to the medial side of prosthesis 10C, the ample margin between the outer limits of medial articular surface 42 and medial edge 74 of peripheral wall 54 allows medial transition radius $R_{TM}$ to be relatively large, thereby allowing such transition to define a relatively large convex profile at lateral edge 72 and medial edge 74 of peripheral wall 54 while still leaving sufficient concave space, constraint and conformity for articular surfaces 40, 42. Lateral transition radius $R_{TL}$ similarly occupies a large margin between the outer limits of lateral articular surface 40 and lateral edge 72 of peripheral wall 54, though the margin is slightly smaller. Therefore, lateral transition radius $R_{TL}$ may be slightly less than medial transition radius $R_{TM}$.

In an exemplary embodiment, medial transition radius $R_{TM}$ is at least zero mm or 0.45 mm and may be as large as 3 mm, 5 mm or 7 mm, or may be any value within any range defined by any of the foregoing values. Lateral transition radius $R_{TL}$ is at least zero mm or 0.5 mm and may be as large as 2 mm, 5 mm or 7 mm, or may be any value within any range defined by any of the foregoing values.

In addition to radii $R_{TM}$, $R_{TL}$ the respective transitions from lateral and medial articular surfaces 40, 42 to lateral and medial edges 72, 74 may also be expressed with reference to the arc length defined by radii $R_{TM}$, $R_{TL}$. Moreover, a longer arc length results in an increasingly broad, convex lateral and medial transition, which in turn provides a large contact area for soft tissue. For example, if an adjacent soft tissue structure (e.g., the IT band or medial collateral ligament) comes into contact with tibial bearing component 14, minimal contact pressures therebetween are experienced if large arc lengths are provided. In an exemplary embodiment, the medial arc length may be as little as 0 mm or 0.83 mm and may be as large as 6.4 mm, or may be any value within any range defined by any of the foregoing values. Lateral arc length may be as little as zero mm or 0.9 mm and may be as large as 3.5 mm or 6.4 mm, or may be any value within any range defined by any of the foregoing values.

Further, the anterolateral "pull back" of the anterior-lateral corner of prosthesis 10, described above, allows the corresponding anterior-lateral corner of bearing component 14 to maintain separation from the IT band through a wide range of flexion, such that only very low contact pressures are present in the limited circumstances where contact may occur.

Prosthesis 10C shown in FIG. 3C is similar to prostheses 10, 10A, 10B described above, and reference numbers in FIGS. 3C and 3D refer to analogous structures shown in FIGS. 1A through 3B, 4A and 4B and described above with respect to prostheses 10, 10A and 10B. Moreover, it should be appreciated that the features described herein with respect to any of prostheses 10, 10A, 10B may be applied to each of the prostheses described herein.

For example, in the illustrative embodiment of FIG. 3C, tibial bearing component 14C includes spine 45 extending proximally from superior surface 38 rather than eminence 44. As noted above, spine 45 is appropriate for use in a posterior-stabilized (PS) prosthesis. Large transition radii $R_T$ may be provided on PS designs as shown, or on CR designs.

Tibial prosthesis 10 (inclusive of tibial prostheses 10A, 10B and 10C) can be considered "soft tissue friendly" because the edges of tibial bearing component 14 and tibial plate 18, including chamfers 32, 50, are smooth and rounded, so that soft tissue coming into contact with these edges will be less likely to chafe or abrade. Further, the high congruence peripheral wall 54 of bearing component 14 and peripheral wall 25 of baseplate 12 provides coverage of nearly all of superior surface 34 of baseplate 12 with bearing component 14, thereby preventing contact between any soft tissue and any metal edge of baseplate 12. Instead, where contact does occur, it is with the soft, polymeric edges of tibial bearing 14 or with the flat or gently convex surfaces of chamfers 32, 50.

3. Trial Tibial Prostheses

As noted above, a kit of tibial prosthesis 10 may be provided with a variety of sizes and configurations to accommodate different bone sizes and geometries. The choice of one particular size may be planned preoperatively such as through preoperative imaging and other planning procedures. Alternatively, an implant size may be chosen, or a previous size choice modified, intraoperatively. To facilitate proper intraoperative selection of a particular size for tibial prosthesis 10 from among a range of available sizes, and to promote proper orientation of the chosen prosthesis 10, tibial prosthesis 10 may be part of a kit including one or more template or "trial" components.

Figure 5:
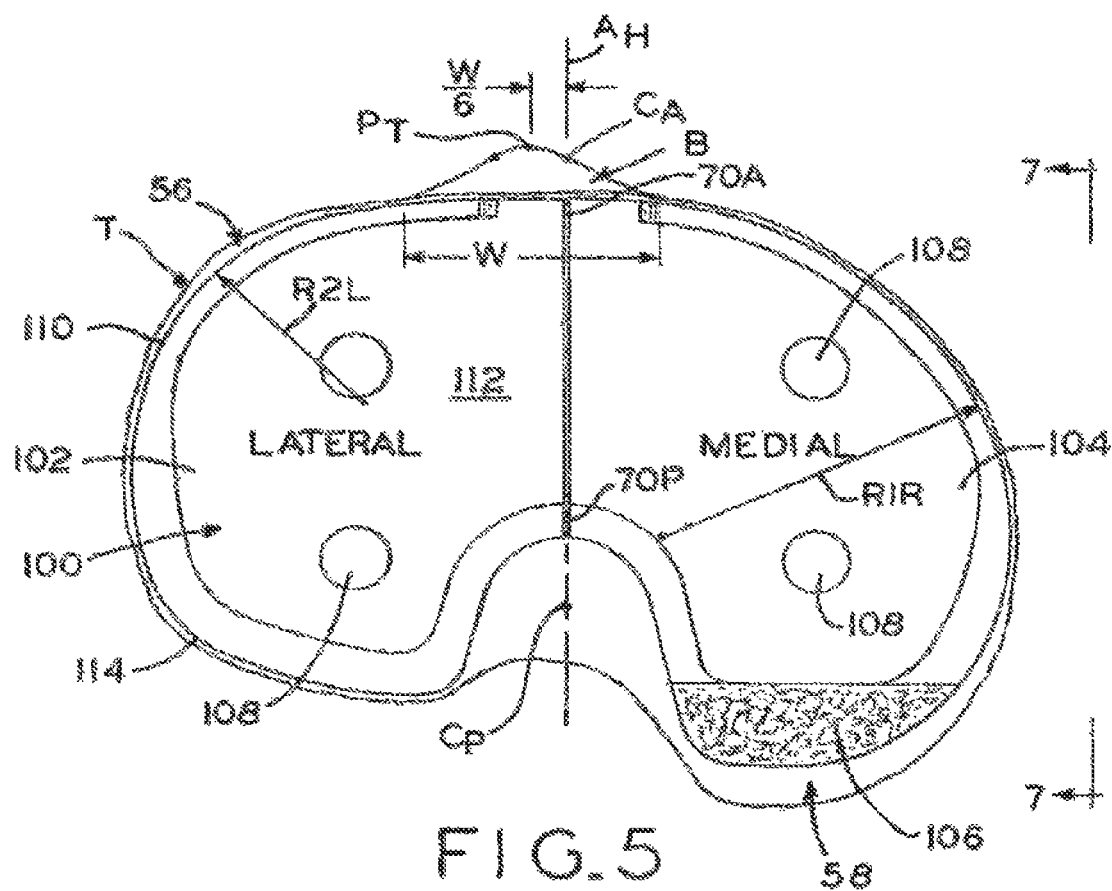
FIG. 5 is a top plan view of the resected proximal tibial surface shown in FIG. 2A, with a properly sized tibial trial component thereon.
Figure 6:
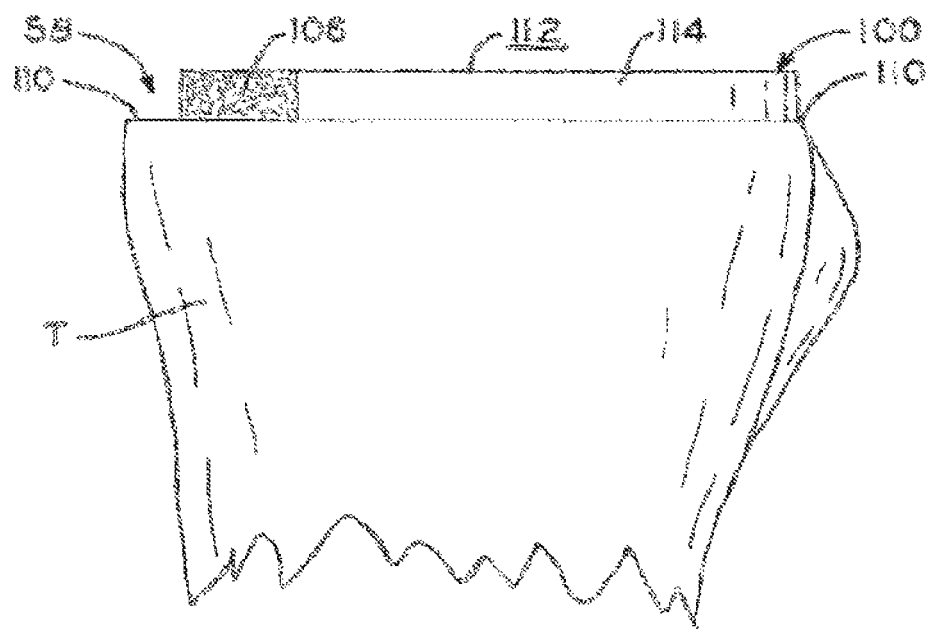
FIG. 6 is a side, elevation view of the tibia and trial component shown in FIG. 2A.

Referring now to FIGS. 5 and 6, trial prosthesis 100 may be temporarily coupled to tibia T for intraoperative sizing evaluation of tibial prosthesis 10 and initial steps in the implantation of tibial prosthesis 10. Trial prosthesis 100 is one of a set of trial prostheses provided as a kit, with each trial prosthesis having a different size and geometrical configuration. Each trial prosthesis in the set of trial prostheses corresponds to one among several sizes of permanent prosthesis 10, such as to varying peripheries 200 of tibial baseplate 12 as described above.

For example, as shown in FIG. 5, trial prosthesis 100 defines superior surface 112 generally corresponding in size and shape to periphery 200 of tibial plate 18, and including lateral portion 102 and medial portion 104. Like periphery 200, superior surface 112 is asymmetrical about home axis $A_H$, with lateral portion 102 having a generally shorter overall anteroposterior extent as compared to medial portion 104 (in part because medial portion 104 includes void indicator 106 as discussed below). In addition, the anterolateral "corner" of lateral portion 102 defines radius $R_1$, which is identical to radius $R_1$ of periphery 200, while the anteromedial "corner" of medial portion 104 defines radius $R_2$, which is identical to radius $R_2$ of periphery 200 and is therefore greater than radius $R_1$.

Moreover, trial prosthesis 100 includes perimeter wall 114 which defines a substantially identical periphery as peripheral wall 25 of tibial plate 18, and therefore has the same geometrical features and shapes of periphery 200 described above with respect to tibial plate 18. Thus, the nature of the asymmetry of trial prosthesis 100 changes across the various sizes of tibial prosthesis provided in the kit including trial prosthesis 100.

In an alternative embodiment, a trial prosthesis may be provided which is designed to extend completely to the posterior-medial edge of the natural tibial resection periphery. Thus, such a trial would substantially completely cover the resected tibial surface, thereby aiding in determination of a proper rotational orientation of the trial (and, therefore, of the final tibial baseplate 12). In this alternative embodiment, the trial prosthesis lacks the posterior-medial "pull back" of tibial plate 18, described above, and therefore does not define void 58.

Trial prosthesis 100 includes void indicator 106 disposed at the posterior portion of medial portion 104, which occupies a given particular area of superior surface 112 and peripheral wall 114 corresponding to chamfer 32 of baseplate 12. Specifically, void indicator 106 indicates that portion of baseplate 12 where chamfer 32 is left exposed after tibial bearing component 14 attached to baseplate 12. Thus, void indicator 106 provides a visual marker for the ultimate location of relief 52 (discussed above) with respect to tibia T after implantation of tibial prosthesis 10.

Void indicator 106 advantageously facilitates proper rotational and spatial orientation of trial prosthesis 100 on the resected proximal surface of tibia T by allowing a surgeon to visually match tibial bearing component 14 with trial prosthesis 100, as described in detail below. In the illustrated embodiment, void indicator 106 is an area of visual and/or tactile contrast with the remainder of tibial plate 18. This contrast may include, for example, a contrasting color, texture, surface finish, or the like, or may be formed by a geometric discrepancy such as a step or lip, for example.

Referring specifically to FIG. 3, trial prosthesis 100 further includes a plurality of peg hole locators 108 corresponding to the proper location for peg holes in tibia T to receive pegs (not shown) extending inferiorly from tibial plate 18 of tibial baseplate 12. Advantageously, peg hole locators 108 allow a surgeon to demarcate the appropriate location on the resected proximal surface of tibia T for peg hole centers after the proper size and orientation for trial prosthesis 100 has been found. The marked peg hole centers facilitating eventual drilling of properly located peg holes in tibia T after trial prosthesis has been removed, as discussed in detail below. Alternatively, peg hole locators 108 may be used as drill guides to drill appropriately positioned peg holes while trial prosthesis 100 is still positioned on tibia T. As an alternative to peg hole locators 108, it is contemplated that a central aperture may be provided as a keel or stem locator for demarcating the proper location of keel 16 (FIG. 3A).

Void indicator 106 may also be used to demarcate the implanted position and location of a baseplate which is symmetric, or has any other periphery which is different from periphery 200. In some instances, for example, it may be desirable to use a tibial baseplate different from baseplate 12. However, the advantages conferred by the asymmetric periphery of baseplate 12, such as proper rotational orientation and positioning, may still be realized. Asymmetric trial prosthesis 100 may be used to locate the proper location for peg holes or a keel, as discussed herein, with void indicator 106 offering a visual indication of which part of the resected proximal surface of tibia T will not be covered over by the differently-shaped tibial baseplate. When the tibial baseplate is implanted, it will have the same advantageous rotation/location as baseplate 12 even if the differently-shaped baseplate covers less bone. The surgeon will also be assured that those areas of bone not covered by the differently-shaped prosthesis are proper, having previously seen such areas covered by void indicator 106.

4. Tibial Prosthesis Implantation

In use, a surgeon first performs a resection of tibia T using conventional procedures and tools, as are well-known in the art. Exemplary surgical procedures and associated surgical instruments are disclosed in "Zimmer LPS-Flex Fixed Bearing Knee, Surgical Technique," "NEXGEN COMPLETE KNEE SOLUTION, Surgical Technique for the CR-Flex Fixed Bearing Knee" and "Zimmer NexGen Complete Knee Solution Extramedullary/Intramedullary Tibial Resector, Surgical Technique" (collectively, the "Zimmer Surgical Techniques"), copies of which are submitted on even date herewith, the entire disclosures of which are hereby expressly incorporated by reference herein.

In an exemplary embodiment, a surgeon will resect the proximal tibia to leave a planar surface prepared for receipt of a tibial baseplate. For example, the surgeon may wish to perform a resection resulting in a tibial slope defined by the resected tibial surface, which typically slopes proximally from posterior to anterior (i.e., the resected surface runs "uphill" from posterior to anterior). Alternatively, the surgeon may instead opt for zero tibial slope. Varus or valgus slopes may also be employed, in which the resected surface slopes proximally or distally from medial to lateral. The choice of a tibial and/or varus/valgus slope, and the amount or angle of such slopes, may depend upon a variety of factors including correction of deformities, mimicry of the native/preoperative tibial slope, and the like.

Tibial baseplate 12 is appropriate for use with a tibial slope of as little as zero degrees and as much as 9 degrees, and with a varus or valgus slope of up to 3 degrees. However, it is contemplated that a tibial baseplate made in accordance with the present disclosure may be used with any combination of tibial and/or varus/valgus slopes, such as by changing the angular configuration of keel 16 with respect to bone-contacting surface 35.

With a properly resected proximal tibial surface, the surgeon selects trial prosthesis 100 from a kit of trial prostheses, with each prosthesis in the kit having a different size and geometrical configuration (as discussed above). Trial prosthesis 100 is overlaid on the resected surface of tibia T. If trial prosthesis 100 is appropriately sized, a small buffer zone 110 (FIG. 5) of exposed bone of resected tibia T will be visible around the periphery of trial prosthesis 100. Buffer zone 110 should be large enough to allow a surgeon to rotate and/or reposition trial prosthesis 100 within a small range, thereby offering the surgeon some flexibility in the final positioning and kinematic profile of tibial prosthesis 10. However, buffer 110 should be small enough to prevent trial prosthesis 100 from being rotated or moved to an improper location or orientation, or from being implanted in such as way as to produce excessive overhang of the edge of trial prosthesis 100 past the periphery of the resected tibial surface. In one exemplary embodiment, for example, buffer zone 110 will be deemed to be appropriate when trial prosthesis 100 can be rotated from a centered orientation by up to +/−5 degrees (i.e., in either direction). In other embodiments, it is contemplated that such rotation may be as much as +/−10 degrees or +/−15 degrees. In still other embodiments, trial prosthesis 100 may substantially completely match the proximal resected surface of tibia T, such that buffer zone 110 is eliminated and no rotational freedom is afforded.

To aid the surgeon in finding proper rotational orientation, trial prosthesis 100 may include anterior and posterior alignment indicia 70A, 70P (FIG. 5). Similarly positioned marks may be provided on tibial plate 18 for reference upon final implantation thereof. The surgeon can align anterior indicium 70A with anterior point $C_A$ and posterior indicium 70P with PCL attachment point $C_P$, thereby ensuring the anatomical and component home axes $A_H$ (described above) are properly aligned. Alternatively, a surgeon may use indicia 70A, 70P to indicate a desired deviance from alignment with home axis $A_H$. As noted above, deviation of up to 5 degrees is envisioned with the exemplary embodiments described herein. A surgeon may choose to orient indicia 70A, 70P to another tibial landmark, such as the middle of the patella or the medial end of tibial tubercle B.

The large coverage of trial prosthesis 100 (and, concomitantly, of tibial plate 18) ensures that tibial baseplate 12 will be properly positioned and oriented on tibia T upon implantation, thereby ensuring proper kinematic interaction between tibial prosthesis 10 and femoral component 60. If buffer zone 110 is either nonexistent or too large, another trial prosthesis 100 may be selected from the kit and compared in a similar fashion. This process is repeated iteratively until the surgeon has a proper fit, such as the fit illustrated in FIGS. 3 and 4, between trial prosthesis 100 and the proximal resected surface of tibia T.

With the proper size for trial prosthesis 100 selected and its orientation on tibia T settled, trial prosthesis 100 is secured to tibia T, such as by pins, screws, temporary adhesive, or any other conventional attachment methods. Once trial prosthesis 100 is so secured, other trial components, such as trial femoral components and trial tibial bearing components (not shown) may be positioned and used to articulate the leg through a range of motion to ensure a desired kinematic profile. During such articulation, void indicator 106 may be used to indicate to the surgeon that any impingement of femoral component 60, femur F or adjacent soft tissues upon trial prosthesis 100 at void indicator 106 will not occur when tibial prosthesis 10 is implanted. Once the surgeon is satisfied with the location, orientation and kinematic profile of trial prosthesis 100, peg hole locators 108 may be used to demarcate the appropriate location of peg holes in tibia T for tibial baseplate 12. Such peg holes may be drilled in tibia T with trial prosthesis 100 attached, or trial prosthesis 100 may be removed prior to drilling the holes.

With tibia T thus prepared for receipt of tibial prosthesis 10, tibial baseplate 12 may be provided by the surgeon (e.g., procured from a kit or surgical inventory), and implanted on tibia T, such that implant pegs (not shown) fit into holes previously identified and created using peg hole locators 108 of trial prosthesis 100. Tibial baseplate 12 may be selected from a family or kit of tibial baseplate sizes to correspond with the chosen size and/or configuration of trial component 100, thereby ensuring that tibial plate 18 will cover a large proportion of the resected proximal surface of tibia T, as trial prosthesis 100 did prior to removal.

In an alternative embodiment, the surgeon may provide a tibial baseplate (not shown) having a periphery that does not match periphery 200 of trial prosthesis 100. For example, the surgeon may choose a baseplate which is symmetric about an anteroposterior axis. In another example, a surgeon may choose a tibial baseplate having the same periphery as tibial bearing component 14, and having a vertical peripheral wall in place of chamfer 32. In this embodiment, void indicator may be configured to show the non-acuity between periphery 200 and the differently-shaped tibial baseplate, as described above. Upon implantation of the differently-shaped tibial baseplate, the surgeon can visually verify that the portions of bone previously covered by void indicator are not covered by the tibial baseplate Tibial baseplate 12 (or an alternative baseplate, as described above) is implanted upon the proximal surface of tibia T in accordance with accepted surgical procedures. Exemplary surgical procedures and associated surgical instruments are disclosed in the Zimmer Surgical Techniques, incorporated by reference above. Tibial baseplate 12 is affixed to tibia T by any suitable method, such as by keel 16 (FIGS. 3A, 3C and 4A), adhesive, bone-ingrowth material, and the like.

With tibial baseplate 12 implanted, tibial bearing component 14 may be coupled with tibial baseplate 12 to complete tibial prosthesis 10, such as by using locking mechanism 26. Once attached, tibial bearing component 14 will leave the posteromedial portion of tibial baseplate 12 uncovered to create relief 52 (as shown in FIG. 7 and discussed above). Thus, a surgeon may wish to verify that this anterior-biased, "asymmetrical" orientation of medial articular surface 42 is proper prior to permanent affixation of tibial bearing component 14 to tibial baseplate 12.

To accomplish such verification, tibial bearing component 14 may be placed side-by-side with trial prosthesis 100, with inferior surface 36 of tibial bearing component 14 in contact with superior surface 112 of trial prosthesis 100. If properly matched with the chosen size and configuration of trial prosthesis 100, inferior surface 36 tibial bearing component 14 will substantially cover superior surface 112, leaving only void indicator 106 exposed. Put another way, peripheral wall 54 of tibial bearing component 14 will trace peripheral wall 114 of tibial trial prosthesis 100, excluding the posteromedial area defined by void indicator 106. If inferior surface 36 of tibial bearing component 14 is a match with superior surface 112 of trial prosthesis 100 except for void indicator 106 (which is left uncovered by tibial bearing component 14), then tibial bearing component 14 is the proper size component.

When the surgeon is satisfied that tibial bearing component 14 is properly matched and fitted to the installed tibial baseplate 12, bearing component 14 is secured using locking mechanism 26 and the corresponding tibial bearing locking mechanism and appropriate instrumentation (not shown). Exemplary methods for employing locking mechanism 26 are described in U.S. provisional patent application Ser. Nos. 61/367,374 and 61/367,375 filed Jul. 24, 2010, and U.S. patent application Ser. Nos. 13/189,324 and 13/189,328 filed Jul. 22, 2011, all entitled TIBIAL PROSTHESIS, the entire disclosures of which are hereby expressly incorporated herein by reference.

Bearing component 14 is not movable with respect to baseplate 12 after the components have been locked to one another, which is to say the embodiments of prosthesis 10 illustrated herein are "fixed bearing" designs. Thus, proper location and rotational orientation of tibial bearing component 14 upon tibial plate 18 is ensured by cooperation between raised perimeter 24 and peripheral recess 46, as well as by locking mechanism 26 cooperating with central recess 47. Such proper orientation results in medial articular surface 42 being generally anteriorly disposed with respect to medial compartment 22 of tibial plate 18, as noted above. It is also contemplated that the principles of the present disclosure may be applied to a "mobile bearing" design in which the tibial bearing component is movable in vivo with respect to the tibial baseplate. In mobile bearing designs, the periphery of the tibial bearing component will generally be smaller than the periphery of the tibial baseplate, similar to certain embodiments described above.

Femoral component 60 may be affixed to a distal end of femur F, as appropriate, using any conventional methods and/or components. Exemplary surgical procedures and instruments for such affixation are disclosed in the Zimmer Surgical Techniques, incorporated by reference above. Femur F and tibia T may then be articulated with respect to one another to ensure that femur F, femoral component 60 and/or adjacent soft tissues do not impinge upon tibial baseplate 12 and/or tibial bearing component 14 in deep flexion, such as at a flexion angle β of 155° as shown in FIG. 7. When the surgeon is satisfied with the location, orientation and kinematic profile of tibial prosthesis 10, the knee replacement surgery is completed in accordance with conventional procedures.

While this invention has been described as having an exemplary design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A tibial prosthesis comprising:
a tibial baseplate comprising
a baseplate inferior surface configured for contacting a bone surface;
an opposing baseplate superior surface defining a medial compartment, a lateral compartment, and a baseplate periphery;
a baseplate anteroposterior axis disposed between said lateral compartment and said medial compartment, said baseplate anteroposterior axis extending from an anterior edge to a posterior edge of said tibial baseplate;
a baselate peripheral wall extending from said baseplate inferior surface to said baseplate periphery; and
said baseplate peripheral wall of said tibial baseplate includes a baseplate chamfer extending from a posterior portion of said medial compartment of said tibial baseplate to said baseplate inferior surface of said tibial baseplate, said baseplate chamfer defining an acute baseplate chamfer angle with said baseplate inferior surface;
a tibial bearing component mountable to said tibial baseplate and comprising:
an bearing inferior surface;
an opposing bearing superior surface defining a lateral articular surface and a medial articular surface;
a bearing anteroposterior axis disposed between said lateral articular surface and said medial articular surface and extending from an anterior edge to a posterior edge of said tibial bearing component; and
a bearing peripheral wall extending from said bearing inferior surface to said bearing superior surface, said bearing peripheral wall having a tibial bearing chamfer extending from a posterior medial edge of said bearing superior surface toward a posterior medial edge of said bearing inferior surface, said tibial bearing chamfer extending across at least 25% of an available proximal/distal distance between said bearing superior and said bearing inferior surfaces, said tibial bearing chamfer forming an acute bearing chamfer angle with said bearing inferior surface such that said bearing chamfer extends proximally and anteriorly from said bearing inferior surface toward said bearing superior surface, wherein said baseplate peripheral wall extends in a posterior direction beyond the posterior medial edge of said bearing inferior surface such that said bearing inferior surface is sized to fit within said baseplate periphery when said tibial bearing component is mounted to said tibial baseplate.

2. The tibial prosthesis of claim 1, wherein said tibial bearing chamfer extends across substantially the entire available proximal/distance.

3. The tibial prosthesis of claim 1, wherein said acute bearing chamfer angle comprises an angle between about 35 degrees and about 75 degrees.

4. The tibial prosthesis of claim 1, wherein said acute bearing chamfer angle comprises an angle of about 61 degrees.

5. The tibial bearing prosthesis of claim 1, wherein said bearing chamfer defines an overall anteroposterior extent, measured in a sagittal plane as an anteroposterior distance along a direction parallel to said anteroposterior axis, of about 2.7 mm.

6. The tibial prosthesis of claim 1, wherein said bearing chamfer defines an overall length, measured in a sagittal plane as a distance from an anterior/proximal end of said bearing chamfer to an opposing posterior/distal end of said bearing chamfer, of at least about 4 mm.

7. The tibial prosthesis of claim 1, wherein said bearing chamfer defines an arcuate profile in a sagittal plane.

8. The tibial prosthesis of claim 7, wherein said bearing chamfer defines a first radius, measured in the sagittal plane, of between about 5 mm and about 180 mm.

9. The tibial posthesis of claim 8, wherein said first radius defines an anteroposterior extent, measured in the sagittal plane as an anteroposterior distance along a direction parallel to said anteroposterior axis, of about 2.0 mm.

10. The tibial prosthesis of claim 8, wherein said bearing chamfer defines a second radius, measured in the sagittal plane, of between about 5 mm and about 180 mm.

11. The tibial prosthesis of claim 10, wherein said first radius defines an anteroposterior extent, measured in the sagittal plane as an anteroposterior distance along a direction parallel to said anteroposterior axis, of about 0.7 mm.

12. The tibial prothesis of claim 1, wherein said bearing chamfer defines a linear profile in a sagittal plane.

13. The tibial prosthesis of claim 1, wherein said tibial bearing component further comprises a lateral chamfer extending from a lateral posterior edge of said superior surface toward said inferior surface.

14. The tibia prosthesis of claim 1, in combination with a femoral component adapted to articulate with said tibial bearing component, a relief defined between said femoral component and said bearing chamfer when said femoral component is configured in a deep flexion orientation with respect to said tibial bearing component.

15. The tibial prosthesis of claim 1, wherein said tibial bearing component further comprises a rounded transition from said medial. articular surface to an adjacent medial edge of said peripheral watt, said rounded transition defining a transition radius of at least about 0.45 mm.

16. The tibial prosthesis of claim 1, wherein said, tibial bearing component further comprises a rounded transition from said medial articular surface to an adjacent medial edge of said peripheral wall, said rounded transition defining an arc length of at least about 0.83 mm.

17. The tibial prosthesis of claim 1, wherein said tibial bearing component further comprises a rounded transition from said lateral articular surface to an adjacent lateral edge of said peripheral wall, said rounded transition. defining a transition radius of at least about 0.5 mm.

18. The tibial prosthesis of claim 1. wherein said tibial bearing component further comprises a rounded transition from said lateral articular surface to an adjacent lateral edge of said peripheral wall, said rounded transition. defining an arc length of at least about 0.9 mm.

19. The tibial prosthesis of claim 1, wherein said baseplate chamfer angle is substantially identical to said bearing chamfer angle of said bearing component, such that said baseplate chamfer and said tibial bearing chamfer cooperate to form a substantially continuous chamfer extending from said baseplate inferior surface to said medial articular surface when said tibial bearing component is mounted to said tibial baseplate.

20. The prosthesis of claim 1, wherein said baseplate chamfer angle comprises an angle between about 35 degrees and about 75 degrees.

21. A tibial prosthesis system, the system comprising:
a tibial baseplate including medial and lateral compartments bounded by a baseplate periphery, said medial compartment including a baseplate peripheral wall and a posteromedial baseplate potion defining a baseplate chamfer, said baseplate chamfer defining an acute baseplate chamfer angle with respect to a coronal plane;
a first tibial bearing component comprising:
a first inferior surface sized to fit within said baseplate periphery;
an opposing first superior surface;
a first medial portion having a first medial articular surface forming part of said first superior surface;
a first lateral portion disposed opposite said first medial portion with respect to a first anteroposterior axis, said first lateral portion having a first lateral articular surface forming another part of said first superior surface; and
a first bearing chamfer extending from a posterior medial edge of said first superior surface toward said first inferior surface, said first bearing chamfer extending across at least 25% of a first available proximal/distal distance between said first superior and first inferior surfaces at said posterior medial edge, said first bearing chamfer defining an acute first bearing angle with respect to said first inferior surface, and said baseplate peripheral wall extending in a posterior direction beyond a first posterior medial edge of said first inferior surface when said first tibial bearing component is mounted to said tibial baseplate; and
a second tibial bearing component comprising:
a second inferior surface sized to fit within said baseplate periphery;
an opposing second superior surface defining a second lateral articular surface and a second medial articular surface; and
a second medial portion having a second medial articular surface forming part of said second superior surface;
a second lateral portion disposed opposite said second medial portion with respect to a second anteroposterior axis, said second lateral portion having a second lateral articular surface forming another part of said second superior surface; and
a second bearing chamfer extending from a posterior medial edge of said second superior surface toward said second inferior surface, said second bearing chamfer extending across at least 25% of a second available proximal/distal distance between said second superior and second inferior surfaces at said posterior medial edge, said second bearing chamfer defining an acute second bearing angle with respect to said second inferior surface, and said baseplate peripheral wall extending in a posterior direction beyond a second posterior medial edge of said second inferior surface when said second tibial bearing component is mounted to said tibial baseplate, wherein said second tibial bearing component is differently sized from said first tibial bearing component.

22. The system of claim 21, wherein:

said first tibial bearing component defines a first overall bearing thickness defined between said first inferior surface and said first superior surface, said differently sized second tibial bearing component defines a second overall bearing thickness defined between said second inferior surface and said second superior surface, and said second overall bearing thickness is greater than said first overall bearing thickness.

23. The system of claim 21, wherein said tibial baseplate comprises a first tibial baseplate, the system further comprising a second tibial baseplate differently sized from said first tibial baseplate, wherein:

said medial portion of first bearing component defines a first overall medial anteroposterior extent, as measured along a direction parallel to said first anteroposterior axis of said first tibial bearing component;

said medial portion of second bearing component defines a second overall medial anteroposterior extent, as measured along a direction parallel to said second anteroposterior axis of said second tibial bearing component; and said second overall medial anteroposterior extent is greater than said first overall medial anteroposterior extent.

24. The system of claim 21, wherein said first bearing angle and said second bearing angle are each defined by a proximal/anterior end of said first bearing chamfer and said second bearing chamfer, respectively, said first bearing angle equal to said second bearing angle.

25. The system of claim 21, wherein said first bearing chamfer defines a first radius, measured in a sagittal plane, and said second bearing chamfer defines a corresponding second radius in the sagittal plane, said first radius different from said second radius.

26. The system of claim 25, wherein said first radius is larger than said second radius.

27. The system of claim 25, wherein both of said first radius and said second radius define a common anteroposterior extent as measured in the sagittal plane.

28. The system of claim 27, wherein said common anteroposterior extent is about 2.0 mm.

29. The system of claim 25, wherein said first bearing chamfer defines a third radius disposed distally of said first radius, and said second bearing chamfer defines a corresponding fourth radius disposed of said second radius, said third radius different from said fourth radius.

30. The system of claim 29, wherein both of said third radius and said fourth radius define a common anteroposterior extent as measured in the sagittal plane.

31. The system of claim 30, wherein said common anteroposterior extent is about 0.7 mm.

* * * * *

UNITED STATES PATENT AND TRADEMARK OFFICE
CERTIFICATE OF CORRECTION

| | | |
|---|---|---|
| PATENT NO. | : 8,591,594 B2 | Page 1 of 1 |
| APPLICATION NO. | : 13/229103 | |
| DATED | : November 26, 2013 | |
| INVENTOR(S) | : Parisi et al. | |

It is certified that error appears in the above-identified patent and that said Letters Patent is hereby corrected as shown below:

In The Claims

In column 22, line 28, in Claim 1, delete "comprising" and insert --comprising:--, therefor In column 22, line 39, in Claim 1, delete "baselate" and insert --baseplate--, therefor In column 23, line 18, in Claim 5, after "tibial", delete "bearing", therefor In column 23, line 33, in Claim 9, delete "posthesis" and insert --prosthesis--, therefor In column 23, line 44, in Claim 12, delete "prothesis" and insert --prosthesis--, therefor In column 23, line 50, in Claim 14, delete "tibia" and insert --tibial--, therefor In column 23, line 58, in Claim 15, after "medial", delete ",", therefor In column 23, line 59, in Claim 15, delete "watt" and insert --wall--, therefor In column 23, line 61, in Claim 16, after "said", delete ",", therefor In column 24, line 2, in Claim 17, delete "transition." and insert --transition--, therefor In column 24, line 4, in Claim 18, delete "claim 1." and insert --claim 1,--, therefor In column 24, line 7, in Claim 18, delete "transition." and insert --transition--, therefor In column 24, line 17, in Claim 20, after "The", insert --tibial--, therefor In column 24, line 24, in Claim 21, delete "potion" and insert --portion--, therefor In column 24, line 56, in Claim 21, after "surface;", delete "and", therefor In column 26, line 26, in Claim 29, after "disposed", insert --distally--, therefor Signed and Sealed this
Twenty-fourth Day of March, 2015

Michelle K. Lee
*Director of the United States Patent and Trademark Office*